(12) United States Patent
Mark et al.

(10) Patent No.: US 10,048,176 B2
(45) Date of Patent: Aug. 14, 2018

(54) SYSTEM AND METHOD OF TAKING AND COLLECTING TISSUE CORES FOR TREATMENT

(71) Applicant: Nico Corporation, Indianapolis, IN (US)

(72) Inventors: Joseph L. Mark, Indianapolis, IN (US); Brian C. Dougherty, Terre Haute, IN (US); Alexandra Schwier, Lawrenceburg, IN (US)

(73) Assignee: Nico Corporation, Indianapolis, IN (US)

( * ) Notice: Subject to any disclaimer, the term of this patent is extended or adjusted under 35 U.S.C. 154(b) by 58 days.

(21) Appl. No.: 14/513,639

(22) Filed: Oct. 14, 2014

(65) Prior Publication Data

US 2015/0031126 A1    Jan. 29, 2015

Related U.S. Application Data

(62) Division of application No. 13/352,069, filed on Jan. 17, 2012, now Pat. No. 9,279,751.

(51) Int. Cl.
*G01N 1/31* (2006.01)
*A61B 9/00* (2006.01)
(Continued)

(52) U.S. Cl.
CPC .......... *G01N 1/31* (2013.01); *A61B 10/0275* (2013.01); *A61B 17/32002* (2013.01);
(Continued)

(58) Field of Classification Search
CPC ........ G01N 1/31; A61B 10/0275; A61B 19/38
See application file for complete search history.

(56) References Cited

U.S. PATENT DOCUMENTS

| 2,044,823 A | 6/1936 | Whiteside |
| D161,178 S | 12/1950 | Waldron |
(Continued)

FOREIGN PATENT DOCUMENTS

| AU | 2011253790 A1 | 1/2012 |
| EP | 0125070 A2 | 11/1984 |
(Continued)

OTHER PUBLICATIONS

PCT International Search Report and Opinion for PCT/US2014/015006 dated Apr. 17, 2014.
(Continued)

*Primary Examiner* — Rene Towa
(74) *Attorney, Agent, or Firm* — Kristin L. Murphy; Brooks Kushman P.C.

(57) ABSTRACT

A tissue cutting device that is especially suited for neurosurgical applications is disclosed and described, as well as alternative systems for tissue preservation and transport. The cutting device includes an outer cannula in which a reciprocating inner cannula is disposed. A tissue collector is also provided and is in fluid communication with the lumen of the inner cannula. A temperature control sleeve may be disposed around the tissue collector to control the temperature of the tissue samples. A preservation system may be supplied that is configured to deliver fluids to tissue samples in the tissue collector. A fluid supply sleeve may be disposed about the outer cannula and is selectively positionable along the length of the outer cannula.

12 Claims, 21 Drawing Sheets

(51) Int. Cl.

| | | |
|---|---|---|
| *A61B 10/02* | (2006.01) | |
| *A61B 90/40* | (2016.01) | |
| *A61B 17/32* | (2006.01) | |
| A61B 18/02 | (2006.01) | |
| A61B 17/3207 | (2006.01) | |
| A61B 17/00 | (2006.01) | |
| A61B 18/00 | (2006.01) | |

(52) U.S. Cl.
CPC .......... *A61B 90/40* (2016.02); *A61B 10/0283* (2013.01); *A61B 17/320783* (2013.01); *A61B 18/02* (2013.01); *A61B 2010/0208* (2013.01); *A61B 2017/00017* (2013.01); *A61B 2017/00977* (2013.01); *A61B 2018/00005* (2013.01); *A61B 2217/005* (2013.01); *A61B 2217/007* (2013.01)

(56) References Cited

U.S. PATENT DOCUMENTS

| | | | |
|---|---|---|---|
| 3,674,031 A * | 7/1972 | Weiche | A61B 18/02 604/20 |
| 4,071,029 A | 1/1978 | Richmond et al. | |
| 4,210,146 A | 7/1980 | Banko | |
| 4,314,450 A | 2/1982 | Pelloux-Gervais | |
| 4,316,473 A * | 2/1982 | Beskin | B01L 7/04 165/154 |
| 4,393,665 A * | 7/1983 | Gardner | B65D 81/3876 215/6 |
| 4,493,698 A | 1/1985 | Wang et al. | |
| 4,650,460 A | 3/1987 | Roizenblatt | |
| 4,704,875 A * | 11/1987 | Kieler | F25D 3/08 220/555 |
| 4,770,654 A | 9/1988 | Rogers et al. | |
| 4,940,061 A | 7/1990 | Terwilliger et al. | |
| 4,974,423 A * | 12/1990 | Pring | F25D 3/14 435/307.1 |
| 4,974,426 A * | 12/1990 | Gomez | A45C 11/20 62/457.7 |
| 5,085,658 A | 2/1992 | Meyer | |
| 5,098,426 A | 3/1992 | Sklar et al. | |
| 5,195,541 A | 3/1993 | Obenchain | |
| 5,403,276 A | 4/1995 | Schechter et al. | |
| 5,411,513 A | 5/1995 | Ireland et al. | |
| 5,415,169 A | 5/1995 | Siczek et al. | |
| 5,456,689 A | 10/1995 | Kresch et al. | |
| 5,643,304 A | 7/1997 | Schechter et al. | |
| 5,669,394 A | 9/1997 | Bergery et al. | |
| 5,772,627 A | 6/1998 | Acosta et al. | |
| 5,782,849 A | 7/1998 | Miller | |
| 5,810,744 A | 9/1998 | Chu et al. | |
| 5,911,701 A | 6/1999 | Miller et al. | |
| 5,916,231 A | 6/1999 | Bays | |
| 5,918,478 A | 7/1999 | Bostic | |
| 5,997,560 A | 12/1999 | Miller | |
| 6,017,354 A | 1/2000 | Culp et al. | |
| 6,024,751 A | 2/2000 | Lovato et al. | |
| 6,032,673 A | 3/2000 | Savage et al. | |
| 6,086,544 A | 7/2000 | Hibner et al. | |
| 6,152,871 A | 11/2000 | Foley et al. | |
| 6,179,829 B1 | 1/2001 | Bisch et al. | |
| 6,245,084 B1 | 6/2001 | Mark et al. | |
| 6,258,111 B1 | 7/2001 | Ross et al. | |
| 6,269,888 B1 | 8/2001 | Schuda et al. | |
| 6,312,441 B1 | 11/2001 | Deng | |
| 6,314,751 B1 * | 11/2001 | Gjersvik | F25D 3/02 62/372 |
| 6,322,549 B1 | 11/2001 | Eggers et al. | |
| 6,328,730 B1 | 12/2001 | Harkrider, Jr. | |
| 6,402,701 B1 | 6/2002 | Kaplan et al. | |
| 6,419,641 B1 | 7/2002 | Mark et al. | |
| 6,491,699 B1 | 12/2002 | Henderson et al. | |
| 6,592,530 B1 | 7/2003 | Farhadi | |
| 6,609,020 B2 | 8/2003 | Gill | |
| D479,455 S | 9/2003 | Waldron | |
| 6,629,986 B1 | 10/2003 | Ross et al. | |
| 6,659,998 B2 | 12/2003 | DeHoogh et al. | |
| 7,019,234 B1 | 3/2006 | Mezhinsky et al. | |
| 7,481,775 B2 | 1/2009 | Weikel, Jr. et al. | |
| 7,572,236 B2 | 8/2009 | Quick et al. | |
| 7,678,552 B2 | 3/2010 | Kornblith | |
| 2001/0037114 A1 | 11/2001 | Dinger et al. | |
| 2002/0103496 A1 | 8/2002 | Harper | |
| 2003/0045811 A1 | 3/2003 | Hinchliffe et al. | |
| 2003/0047434 A1 | 3/2003 | Hanson et al. | |
| 2003/0073980 A1 | 4/2003 | Finlay et al. | |
| 2003/0208136 A1 | 11/2003 | Mark et al. | |
| 2004/0049217 A1 | 3/2004 | Ross et al. | |
| 2005/0027210 A1 | 2/2005 | Miller | |
| 2005/0085798 A1 | 4/2005 | Hofmann et al. | |
| 2005/0103607 A1 | 5/2005 | Mezhinsky | |
| 2005/0154407 A1 | 7/2005 | Simpson | |
| 2005/0277970 A1 | 12/2005 | Norman et al. | |
| 2006/0115385 A1 | 6/2006 | Jon Meyer | |
| 2006/0241343 A1 | 10/2006 | Miller et al. | |
| 2006/0260994 A1 * | 11/2006 | Mark | A61B 10/0275 210/232 |
| 2006/0271014 A1 * | 11/2006 | Hynes | A61M 5/445 604/507 |
| 2007/0073226 A1 | 3/2007 | Polidoro et al. | |
| 2007/0073326 A1 | 3/2007 | Miller et al. | |
| 2007/0149977 A1 | 6/2007 | Heavener | |
| 2007/0213632 A1 * | 9/2007 | Okazaki | A61B 1/012 600/562 |
| 2007/0270714 A1 | 11/2007 | Cushner et al. | |
| 2008/0045964 A1 | 2/2008 | Mishra | |
| 2008/0114387 A1 | 5/2008 | Hertweck et al. | |
| 2008/0188767 A1 * | 8/2008 | Oaki | A61B 1/018 600/566 |
| 2008/0234720 A1 | 9/2008 | Chang et al. | |
| 2008/0243105 A1 | 10/2008 | Horvath | |
| 2008/0249366 A1 | 10/2008 | Gruber et al. | |
| 2008/0249553 A1 | 10/2008 | Gruber et al. | |
| 2008/0262476 A1 | 10/2008 | Krause et al. | |
| 2009/0056369 A1 * | 3/2009 | Fink | F25D 17/02 62/457.4 |
| 2009/0112118 A1 | 4/2009 | Quick, Jr. et al. | |
| 2009/0124975 A1 | 5/2009 | Oliver et al. | |
| 2009/0131819 A1 | 5/2009 | Ritchie et al. | |
| 2009/0171243 A1 | 7/2009 | Hibner et al. | |
| 2009/0281477 A1 | 11/2009 | Mikus et al. | |
| 2010/0152615 A1 | 6/2010 | Mark et al. | |
| 2010/0292607 A1 | 11/2010 | Moore et al. | |
| 2011/0056902 A1 | 3/2011 | Cognard | |
| 2011/0190802 A1 | 8/2011 | Mark et al. | |
| 2011/0281350 A1 | 11/2011 | Schowalter et al. | |
| 2011/0282239 A1 | 11/2011 | Conlon et al. | |
| 2011/0282372 A1 | 11/2011 | Schowalter et al. | |
| 2011/0308271 A1 | 12/2011 | Schryver | |
| 2012/0157879 A1 | 6/2012 | Mark | |
| 2012/0211498 A1 * | 8/2012 | Cognard | 220/592.01 |
| 2013/0211316 A1 | 8/2013 | Wilcox et al. | |

FOREIGN PATENT DOCUMENTS

| | | |
|---|---|---|
| EP | 0497520 A1 | 8/1992 |
| EP | 1201210 A1 | 5/2002 |
| EP | 1714617 A1 | 10/2006 |
| EP | 1815798 A2 | 8/2007 |
| EP | 1859742 A1 | 11/2007 |
| EP | 1915949 A2 | 4/2008 |
| JP | 2006282232 | 10/2006 |
| JP | 2007276817 | 10/2007 |
| WO | 9418894 A1 | 9/1994 |
| WO | 9613845 A1 | 5/1996 |
| WO | 9846147 A1 | 10/1998 |
| WO | 0022994 A1 | 4/2000 |
| WO | 0230303 A1 | 4/2002 |
| WO | 2003045290 A1 | 6/2003 |
| WO | 2006123312 A1 | 11/2006 |
| WO | 2007002230 A1 | 1/2007 |
| WO | 2007005507 A2 | 1/2007 |

(56) References Cited

FOREIGN PATENT DOCUMENTS

| WO | 2007047380 A2 | 4/2007 | |
|---|---|---|---|
| WO | 2007062412 A2 | 5/2007 | |
| WO | 2008023193 A2 | 2/2008 | |
| WO | 2008058157 A2 | 5/2008 | |
| WO | WO 2009043609 A1 * | 4/2009 | ......... A47G 23/0241 |
| WO | 2011146682 A1 | 11/2011 | |

OTHER PUBLICATIONS

PCT International Search Report, from corresponding PCT Patent Application No. PCT/US2013/021938 dated Jul. 9, 2013.
Naylor, Stephen, et al., "Unraveling human complexity and disease with systems biology and personalized medicine." Personalized Medicine (2010).
Article, "Patient-Specific Brain Cancer 'Vaccine' May Help Prevent Recurrence," Health News, US Academic Health Center, University of Cincinnati, (Jul. 9, 2008).
Lesniak, Jaciej S., "Targeted therapy for malignant glioma: neural stem cells," ISSN 1473-7175 (2006).
Human, Katy, "Using personalized vaccines, researchers enlist the immune system to oust tumors," www.curetoday.com (2010).
Park, Alice, "A Shot at Cancer," Time (Sep. 3, 2009).
Publication entitled: "Heavy Duty Foot Potentionmeter," published at www.herga.com, Herga Electric Ltd., Apr. 30, 2009.
Publicaton entitled: "Vacuum Generators, How the E-Vac Works," published in Exair Corporation, Copyright 2009.
Publication entitled: "An Automated Turner Resection Device for Neurological Surgery," authors, Martin L. Lazar, M. D., et al.; published by Texas Neurological Institute at Dallas, (vol. 3, No. 3, 1978).
Publication entitled, "Automated Tumor Extraction Device for Neurological Surgery," by Wang et al.; published by Journal of Clinical Engineer/Apr.-Jun. 1979.
Annex to Form PCT/ISA/206 Communication Relating to the Results of the Partial International Search for PCT/US2009/068329 dated Mar. 5, 2010.
PCT International Search Report for PCT/SU2009/068225 dated Oct. 4, 2010.
D.M. Keller, PhD, "Patients With Newly Diagnosed Glioblastoma Benefit Even From Less Than Total Resection," http://www.medscape.com/viewarticle/721786; (May 13, 2010).
PCT International Search Report dated Aug. 3, 2011 for PCT/US2011/037092.
PCT International Search Report dated Sep. 23, 2011 for PCT/US2009/068329.
Nakano, T., et al., Endoscopic Treatment for Deep-seated or Multiple Intraparenchymal Tumers: Technical Note; Minim Invas Neurosurg (2009).
Compton, C.C.; The Surgical Specimen is the Personalized Part of Personalized Cancer Medicine; Society of Surgical Oncology (2009).
Schlomm, T., et al.: "Marked Gene Transcript Level Alterations Occur Early During Radical Prostatectomy," European Urology 53 (2008) 333-346.
Lin, D.W., et al.; "Influence of Surgical Manipulation on Prostate Gene Expression: Implications fro Molecular Correlates of Treatment Effects and Disease Prognosis," Journal of Clinical Oncology (vol. 24, No. 23, Aug. 10, 2006).
Spruessel, Al., et al., "Tissue ischemia time affects gene and protein expression patterns within minutes following surgical tumor excision," Research Report, Center for Cancer Research at Israelitic Hospital (vol. 36, No. 6, 2004).
Dash, A., et al., "Changes in Differential Gene Expression because of Warm Ischemia Time of Radical Prostatectomy Specimens," American Journal of Pathology, vol. 161, No. 5, (Nov. 2002).
Nishihara, T., et al., "A transparent sheath of endoscopic surgery and its application in surgical evacuation of spontaneous intracerebral hematomas," J. Neurosurg 92: 1053-1055 (2000).
Signoretti, S., et al., "Tissue-Based Research in Kidney Cancer: Current Challenges and Future Directions," Review Clin Cancer Res 2008; 14(12) Jun. 15, 2008.
PCT International Search Report for PCT/US2009/068313 dated Mar. 11, 2010.
Publication entitled: "Extending Your Arthroscopic Reach," published by Smith & Nephew Dyonics, Inc., Feb. 1992.
Publication entitled: "EndoFlex Steerable Nucelotome for Endoscopic Microdisectomy," published by Surgical Dynamics, 1993.
Publication entitled: Nucleotome Flex II for Automated Percutaneous Lumbar Discectomy, published by Surgical Dynamics, 1992.
Publication entitled: "Surgical Technique Nucelotome Micro I for Automated Open Lumbar Discectomy," published by Surgical Dynamics, 1992.
Publication entitled: "Micro II Bendable Nucelotome for Open Lumbar Discectomy," published by Surgical Dynamics, 1993.
Publication entitled: "Positron Emission Tomography-Guided Volumetric Resection of Supratentorial High-Grade Glimoas: A Survival Analysis in 66 Consectuvie Patents" by Benoit J.M. Pirotte, M.D., Ph.D., et al.—Published in Clinical Studies Neurosurgery, vol. 64, No. 3, Mar. 2009.
Publiclation entitled: "New Device Approval—Arista TM AH Absorbable Hemostat—P050038," Published in FDA U.S. Food and Drug Administration, dated Apr. 13, 2009.
Publication entitled: "Precision Begins with a Linemaster Switch," published by Linesmaster Switch Corp. 2000.

* cited by examiner

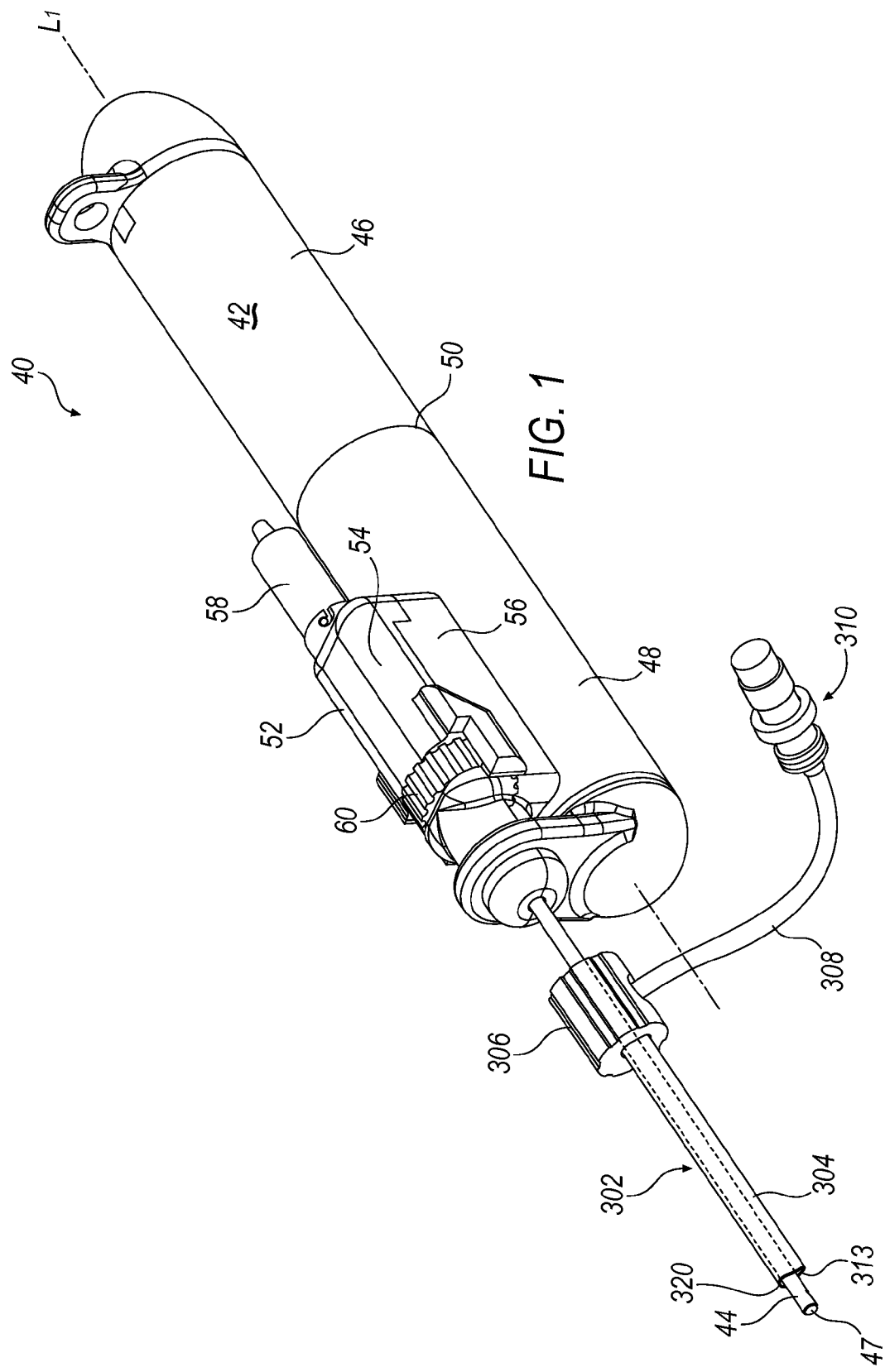

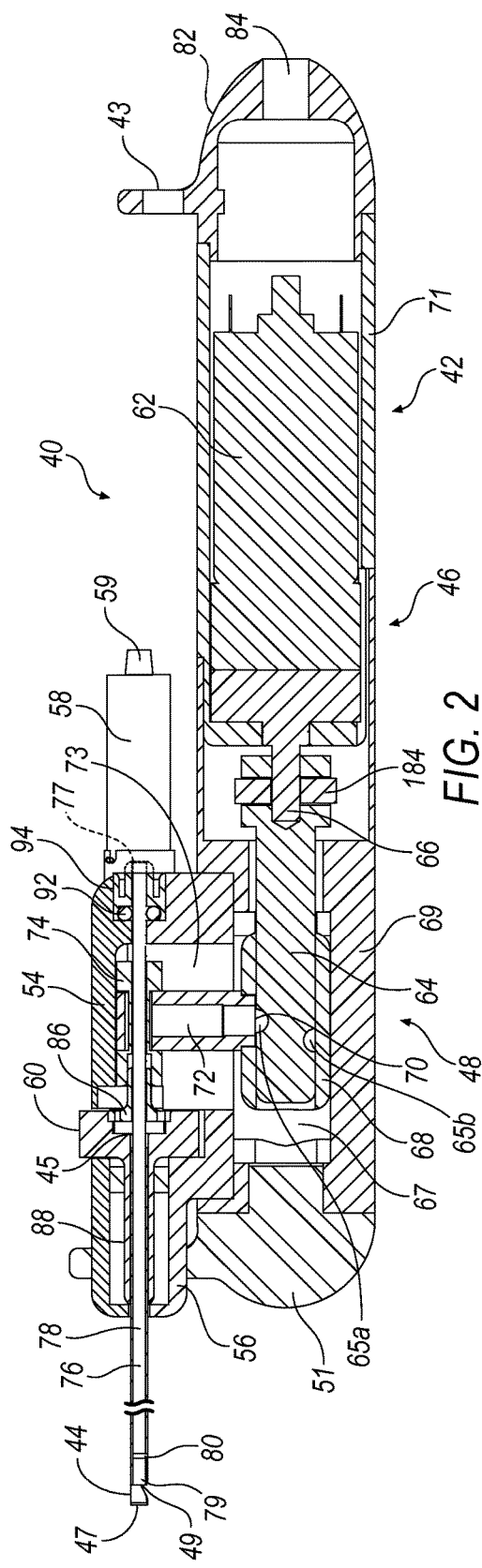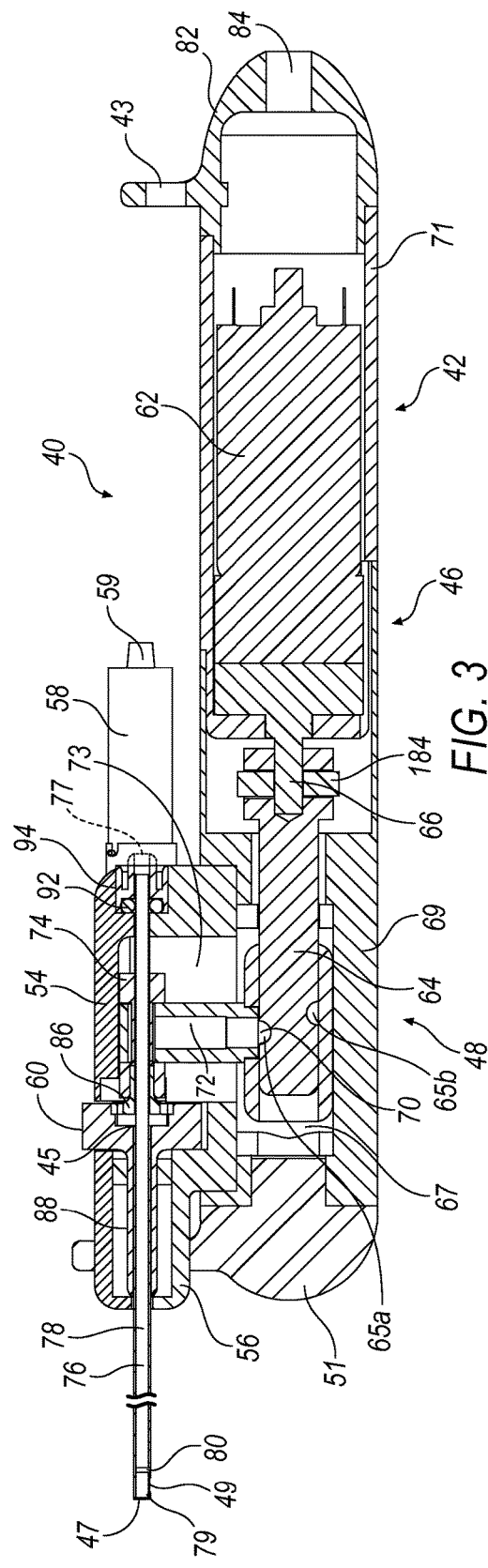

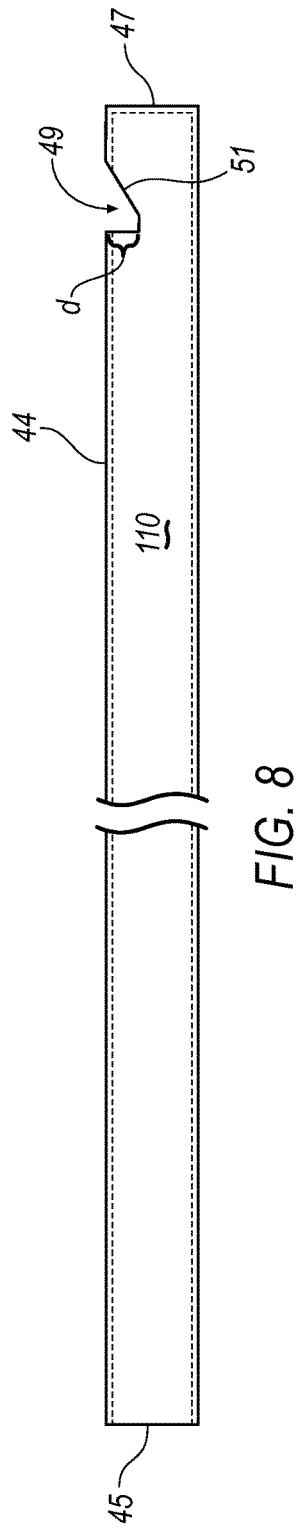
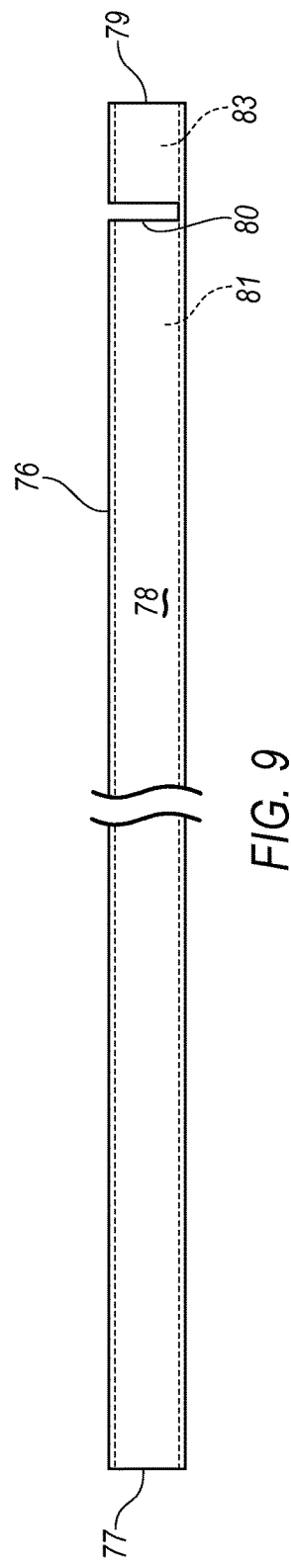
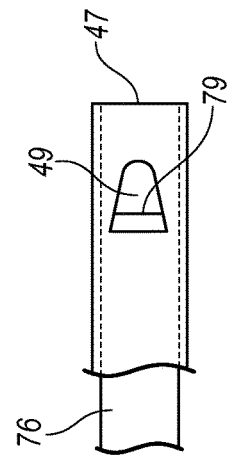
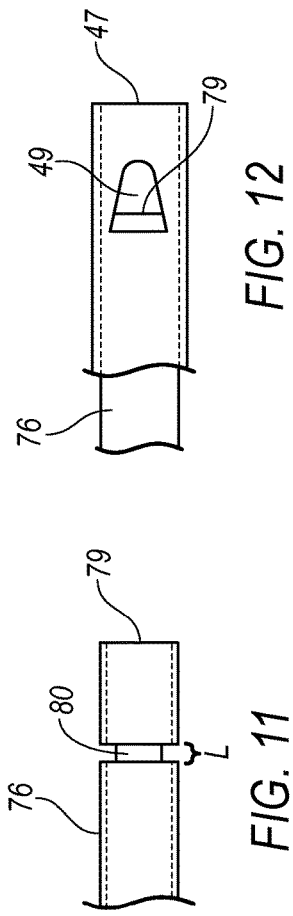
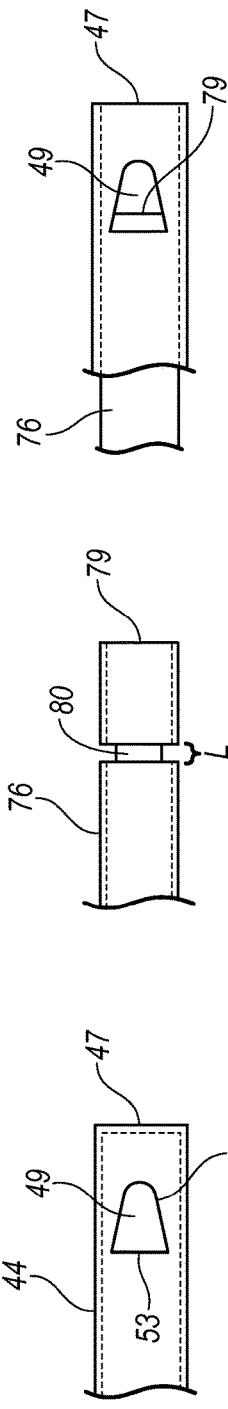
FIG. 8
FIG. 9
FIG. 11
FIG. 12
FIG. 10

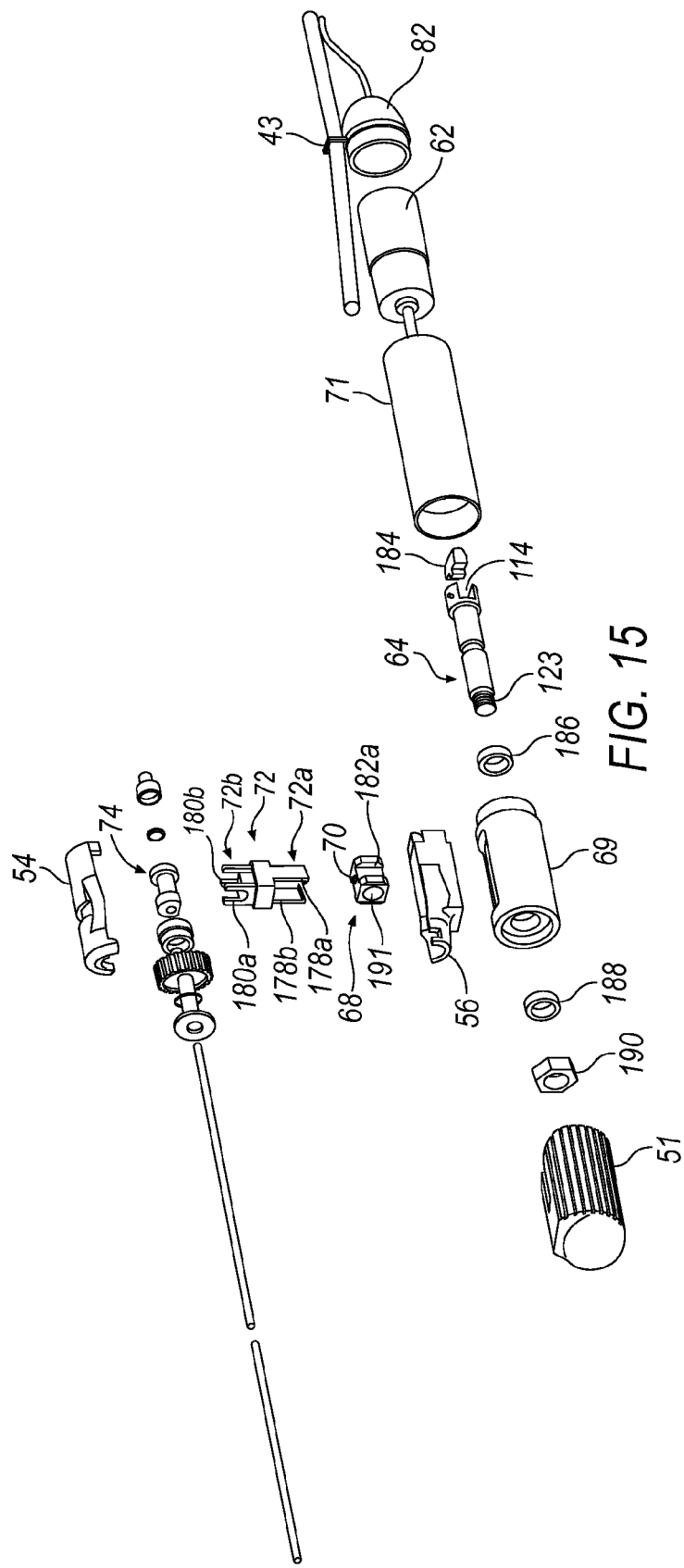

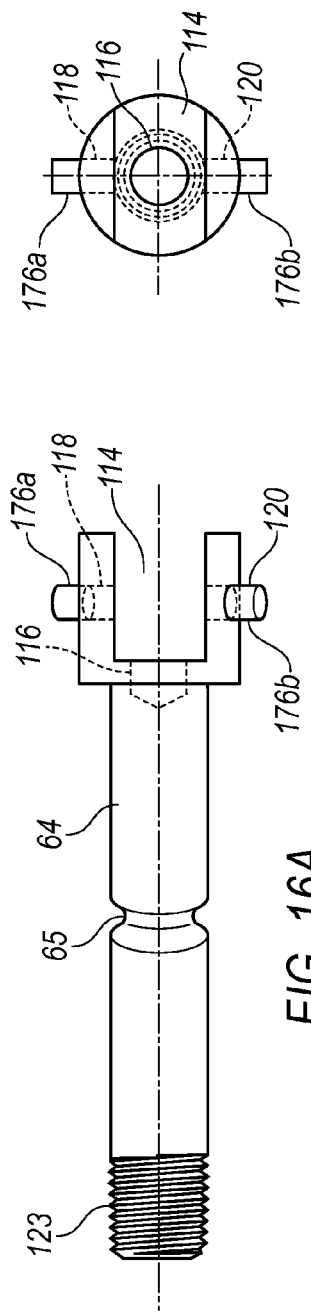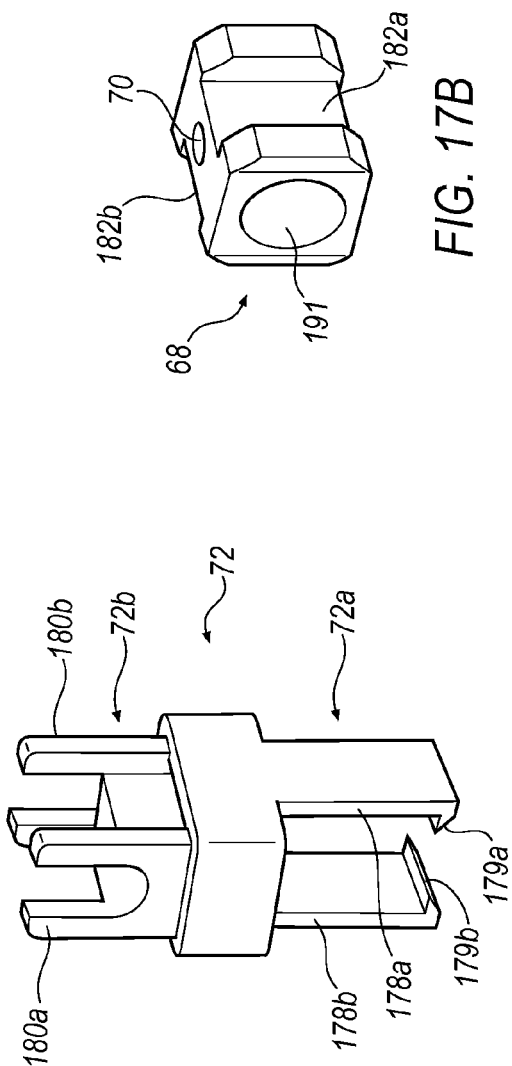

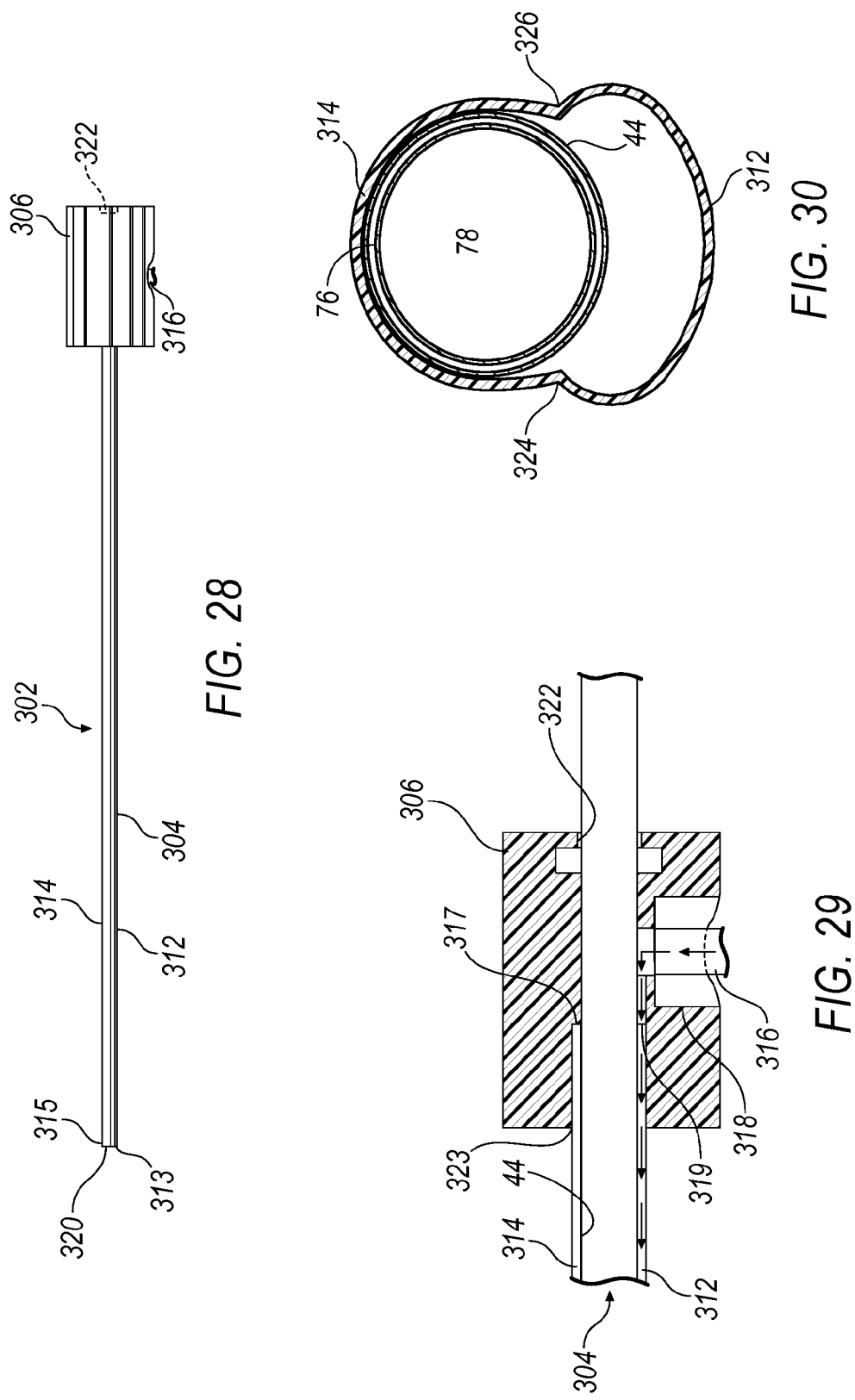

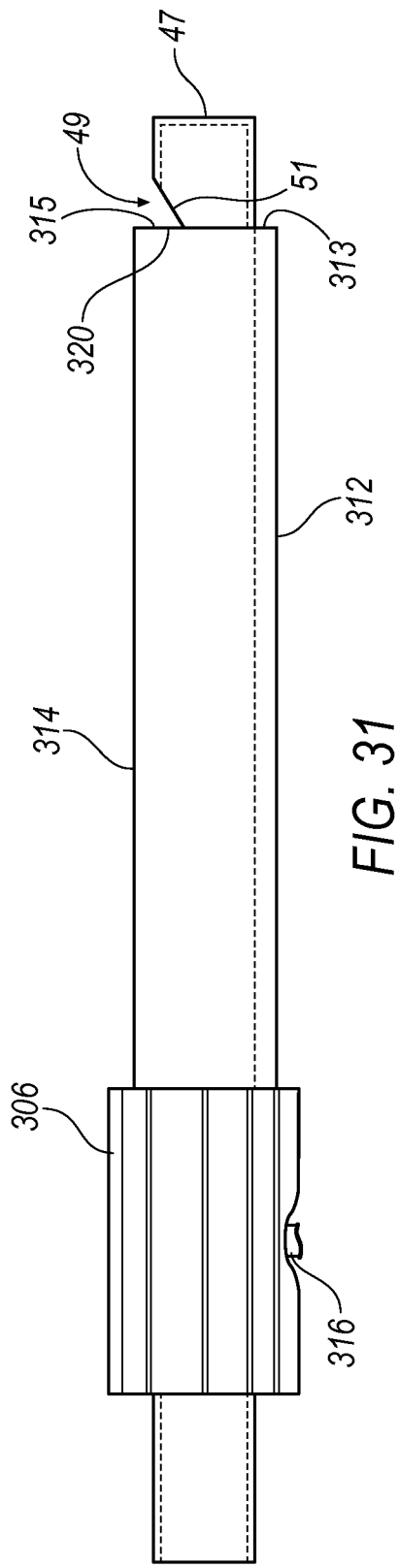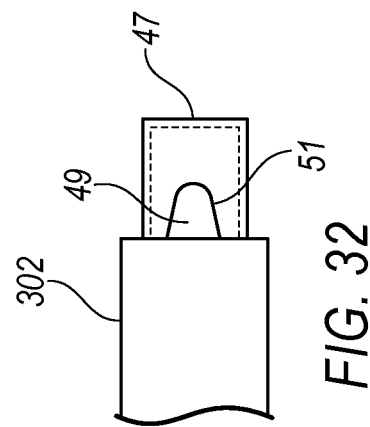
FIG. 31
FIG. 32

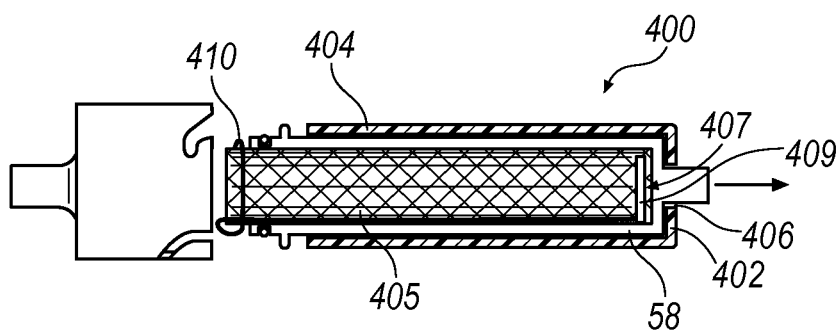
FIG. 33A
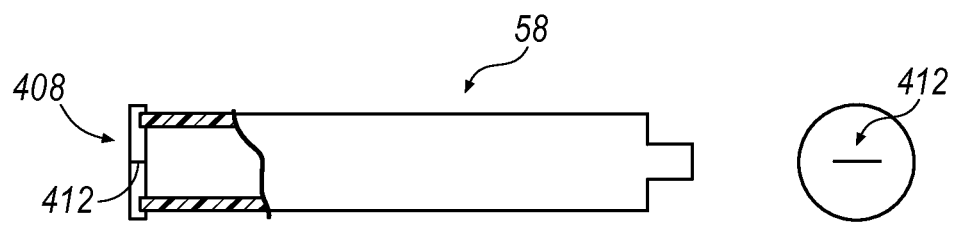 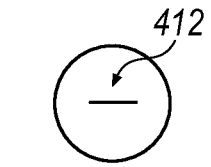
FIG. 33B    FIG. 33C
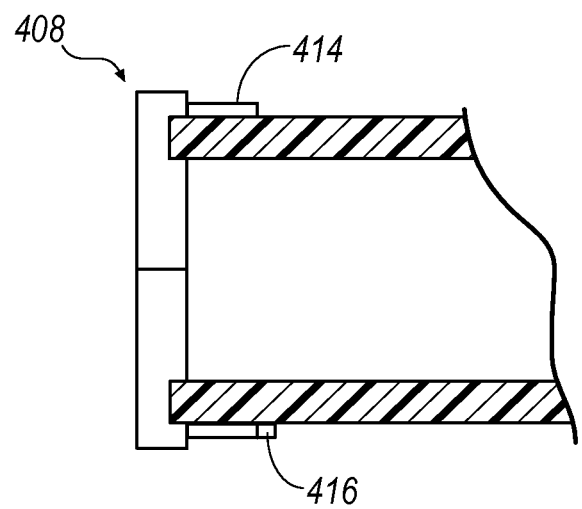
FIG. 33D

SYSTEM AND METHOD OF TAKING AND COLLECTING TISSUE CORES FOR TREATMENT

CROSS-REFERENCE TO RELATED APPLICATIONS

This application is a divisional application of U.S. application Ser.No. 13/352,069, which is continuation-in-part of U.S. application Ser. No. 12/475,258, which is a continuation-in-part of U.S. application Ser.No. 12/435,724, filed on May 5, 2009, now U.S. Pat. No. 8,460,327 issued on Jun 11, 2013, which is a continuation-in-part of U.S. application Ser. No. 12/404,407, filed on Mar. 16, 2009, now U.S. Pat. No. 8,496,599 issued on Jul. 30, 2013, which is a continuation-in-part of U.S. application Ser. No. 12/391,579, filed on Feb. 24, 2009, now U.S. Pat. No. 8,702,738 issued on Apr. 22, 2014, which is a continuation-in-part of U.S. application Ser.No. 12/389,447, filed on Feb. 20, 2009, which is a continuation-in-part of U.S. application Ser. No. 12/336,054, filed Dec. 16, 2008, now U.S. Pat. No. 8,430,825 issued on Apr. 30, 2013, and U.S. application Ser. No. 12/336,086, filed Dec. 16, 2008, now U.S. Pat. No. 8,657,841 issued on Feb. 25, 2014, each of which is hereby incorporated by reference in its entirety.

TECHNICAL FIELD

The present disclosure relates to a system and method for resecting and capturing the resected tissue, while maintaining that tissue within a sterile surgical environment so that the resected tissue may be utilized in the creation of targeted, patient specific treatment purposes, such as personalized medicine.

BACKGROUND

Various abnormalities of body's bodily systems, including the neurological system, can cause severe health risks to patients afflicted by them. For example, in connection with a neurological system, abnormalities such as brain and spinal tumors, cysts, lesions, or neural hematomas can lead to deterioration in motor skills, nausea or vomiting, memory or communication problems, behavioral changes, headaches, or seizures. In certain cases, resection of abnormal tissue masses is required. However, given the various complexity and importance of various bodily functions where the abnormality may be found, such procedures may be extremely delicate and must be executed with great precision and care.

Various tissue removal systems are known or have been proposed for excising abnormal tissue from healthy tissue. However, many known tissue cutting devices suffer from an inability to precisely and atraumatically remove neurological tissue without causing damage to the tissue to be removed, as well as to the surrounding tissues which tissues to be removed are connected or attached to. This "traction" or pull on the surrounding collateral tissue and structures can cause unintended damages to the surrounding tissue. Additionally, various other tissue removal systems use ablative, disruptive or thermal energy, or a combination of these, which cause damage to the excised tissues, as well as the substrate and collateral tissue healthy tissues. Further, some prior art devices also do not provide for successive excision of tissue samples without removal of each tissue sample between each resection cycle.

Damage to the surrounding tissue can also damage the substrate from which the diseased tissue is excised which is also the "receptor bed" for the delivery and uptake by in-situ tissues for personalized medicine regimens. In addition, many known devices are not configured to both "debulk" large volumes of tissue rapidly near clinically important structures or tissues, as well as be able to finely shave on a cellular layer by layer allowing for control, on or around, more delicate structures, such as vessels, nerves, and healthy tissue. Therefore, the prior art devices lack the flexibility as one instrument, which is required in most neurological procedures. Indeed, many prior art devices simply provide for a ripping or tearing action that removes diseased tissue away from the patient. While some prior art instruments are capable of tissue removal via shaving, these instruments are powered by ablative energy sources. Accordingly, these tissue removal mechanisms are not suitable for use when the integrity and viability of the tissue is desired to be maintained for subsequent use for the formulation of personalized medicine regimens. Nor do they allow for the capture and preservation of the resected tissue within a sterile environment. Additionally, the ablative energy that these devices generate also effects the collateral tissue, such as the substrate from which the tumor has been resected which causes the substrate to be damaged and less or even non-effective as a "receptor bed" for subsequent in-situ personalized medicine regimens.

Once diseased tissue is removed, traditionally patients are treated with a "one-size" fits all approach which typically includes a generic and heavy chemotherapy protocol regimen which is delivered to the entire body and designed to provide a balance between enough poison to kill the cancerous tissue without killing all of the healthy tissue. High doses and multiple exposures to radiation are also typically used and delivered by products such as the Gamma Knife and Cyber Knife. However, such invasive treatment regimens are often nothing more than a series of "experiments" on the patient in an effort to find an effective treatment plan. Accordingly the patient must be monitored to ascertain the effectiveness of the generic therapeutic regimen and continuous modification and tweaking of the treatment regime is performed based upon the positive or negative results of each of the previous successes or failures while attempting to balance the sparing of healthy tissues and poisoning effect of the treatment process on the whole patient. Such a treatment regime effectively results in the patient being a guinea pig until an effective treatment regime is achieved to manage the disease or in most cases the patient dies from the disease. Unfortunately, in the case of brain cancers, the patient often succumbs to the disease before an effective treatment regime is achieved. Regardless of these heroic clinical efforts that are very biologically caustic to the patient, rarely are any of the current treatment paradigm curative. In fact, since patients diagnosed with brain cancers often do not typically live beyond 9-14 months after initial diagnosis of the disease, long term clinical implications of whole body chemo or target directed radiation therapy are unknown in these patients and may be detrimental if the patient lived long enough for the true impact to be understood.

However, currently evolving treatment protocols for certain diseases calls for patient specific targeted therapies, i.e., personalized medicine. Several forms of personalized medicine utilize diseased tissue from the patient, i.e., excised tissue, to obtain information about the general disease type, as well as the specific genetic and molecular make-up of the patient's specific disease. From this information, a targeted or personalized oncological treatment regime may be developed that requires the use of the patient's own tissue, which is cultured and used to create a patient specific "cocktail" which may then be delivered back into the patient as a tailored specific therapy regime for that patient.

For effective treatment protocols to be developed, the tissue resected from the patient must be removed, collected and transported in a way that does not compromise the biological integrity or efficacy of the tissue so that it may be not only analyzed by pathology but so further oncological processing may be performed on the tissue so that a patient specific therapeutic cocktail may be created. Traditionally, pathologists only receive limited quality tissue samples and/or limited amounts of tissue due to tissue being damaged during the removal process, or that only a small amount of tissue was able to be retrieved. Tissues for pathological evaluation usage are not required to be maintained in a sterile or aseptic format once removed from within a sterile field, nor was biological integrity or efficacy required. The only requirements were that the tissue not be crushed beyond recognition and not dehydrated. However, for certain types of personalized medicines to be effectively created, there must be sufficient tissue harvested from the tumor and available to an oncological lab (vs. a pathology lab), it must be biologically active and intact, while maintained in a sterile or aseptic environment so that it is not contaminated by foreign matter or biological elements such as bacteria, fungus, etc. This uncompromised environment allows for the effective subsequent culturing of tissue thus allowing the creation of a specific patient therapeutic regimen that enables the creation of personalized medicine therapies. More specifically, there must be an adequate volume of tissue harvested from the tumor, maintained in a sterile or aseptic environment that allows for the resected tissue to be divided for further use as tissue that may be effectively cultured. In some cases it is preferable that the resected tissue be presented to pathology or for oncological processing in predefined consistent sized samples. This offers the opportunity for less manual handling at the point of lab processing of the tissue and therefore less inadvertent physical to the tissue architecture damage which further impacts the true yield of tissue available for pathological or oncological use. Another benefit is that it provides pathology more discreet units for evaluation rather than an en-bloc presentation to pathology (where the en-bloc tissue may only be divided up a few times) of tissue thereby enabling a more complete evaluation of more samples which may produce a more effective evaluation from more of the tumor material. In the case of oncological processing for the creation of patient specific chemotherapy, the tissue samples are first analyzed by pathological means for the determination of specific types of tumor information. Once determined, the tissue, which has been maintained in a sterile or aseptic environment, is then plated for culturing and a variety of different "chemical cocktails" of varying degrees of intensity and composition may be applied to determine which "cocktail" provides the most effective "kill" to the cancer and the least amount of damage to healthy tissue. This procedure is typically referred to as "targeted chemotherapy." An example of the screening of such candidate therapeutic or chemotherapeutic agents for efficacy as to a specific patient is described in U.S. Pat. No. 7,678,552, which is assigned to Precision Therapeutics, Inc. (Pittsburgh, Pa.), the contents of which are incorporated herein by reference in its entirety.

Another emerging therapy that has been developed is immunotherapy treatments. Immunotherapy treatments utilize the immune system of the patient to fight disease. Generally, such treatments involve harvesting antigen presenting tissue and/or cells from the patient and incubating the tissue/cells containing the antigen of the specific diseased being targeted. The antigen presenting cells swallow up the disease antigen and present the antigen on its surface. The antigen presenting cells are then placed in-situ back into the patient to boost and/or function to train the body's own T-cells to attack any cells that display the disease antigen. Additionally, there are other forms of treatment regimes that use the patient's own tumor cells and tissues, which have been cultured to create specific cocktails to be delivered in-situ which are viral based vectors. An example of one company employing such a technique is Tocagen, Inc. (San Diego, Calif.).

The current challenge for prior art tissue cutting devices is the ability to achieve a safe and effective Gross Total Resection (GTR) or near GTR, to provide the lab with intact segments (biopsy quality tissue, not just cells or macerated tissue) of patient's tissue with little to no crush artifact. Consistency in the "bite" size of the resected tissue is also a challenge. Same or near same sized dimensionally resected tissue bites would minimize post processing handling for oncological use and culturing. A slurry of cells or macerated tissue is not very useful for pathology and unacceptable for an effective oncologically based treatment protocol when tissue culturing is required, current resection techniques and devices do not effectively deliver what is required.

The tissue resected by the surgeon and analyzed by the pathologist is the source of crucial information and that same tissue is used to create from the patient's own tissues the appropriately effective treatment protocol to be used. Indeed, the surgically resected tissue possesses the molecular information needed to define the specific molecular characteristics of the patient's tumor, the specific therapies to which the tumor would be expected to respond, and even the specific risks of adverse reactions to given therapies predicted by the patient's genetic make-up.

However, safeguarding the molecular integrity and efficacy of the resected tissue while in the operating room and during transport to the laboratory, is currently a challenge. Tissue samples react to physiological stress. For example, once successfully resected, the specimen may spend varying amounts of time in a biologically unfriendly environment such as at room temperature in the surgical suite and/or holding unit, allowed to be exposed to atmosphere, allowed to dry out, placed in a non-sterile/non-aseptic environment, etc. before being delivered to the laboratory. Temperature may alter the molecular composition and quality of the tissue samples. Similarly, other physiological stress may also detrimentally impact the tissue samples, such as perfusion and oxygenation.

Immunotherapy treatments require biologically active tissue that are tissue blocks, not just individual cells. In fact, it is known that individual cells from diseased tissue respond and act biologically differently than do "colonies" (blocks) of tissue when subjected or exposed to therapeutic agents. Thus tissue must be resected without crush artifact, ablative destruction of the cell walls or thermal damage, such as char, for the benefit of pathological evaluation and for use in personalized medicine oncological therapies. Additionally, it is not just the viability of the resected tissue that must be considered but also the substrate from which the resected tissue has been harvested that also must be respected and not damaged so that it may act as an effective receptor bed for personalized medicine therapeutic regimens that require in-situ placement of the regimen. Moreover, these treatment regimens also require a minimum volume of tissue for effective use. Finally, the tissue that is resected, collected, transported, must be preserved in an aseptic or preferably a sterile environment which precludes dehydration, contamination or compromise so it may remain biologically active and efficacious so that it may be cultured (i.e., living and biologically active tissue that is not compromised with contamination) for additional/advanced pathology based tissue testing and the needs of further processing to accomplish the needs of neuro-oncology and neuro-immunology for targeted therapies such as chemo, viral and other immune therapies for the achievement of personalized medicine.

Thus, a need has arisen for a system that utilizes a tissue cutting device that addresses the foregoing issues, as well as a system that provides for effective transport of resected tissue while minimizing, if not eliminating detrimental stress on the tissue samples.

BRIEF DESCRIPTION OF THE DRAWINGS

Embodiments of the present disclosure will now be described by way of example in greater detail with reference to the attached figures, in which:

FIG. 1 is a perspective view of a tissue cutting device including a fluid supply sleeve in accordance with a first embodiment;

FIG. 2 is a cross-sectional view of the tissue cutting device of FIG. 1 depicting an inner cannula in a first relative position with respect to an outer cannula in which the inner cannula's distal end is located proximally of the outer cannula's distal end;

FIG. 3 is a cross-sectional view of the tissue cutting device of FIG. 1 depicting the inner cannula in a second relative position with respect to the outer cannula in which the inner cannula's distal end is located at the distal end of the outer cannula;

FIG. 8 is a broken side elevation view of the outer cannula of the tissue cutting device of FIG. 1;

FIG. 9 is a broken side elevation view of the inner cannula of the tissue cutting device of FIG. 1;

FIG. 10 is a top plan view of a portion of the outer cannula of the tissue cutting device of FIG. 1 with the inner cannula removed from the outer cannula;

FIG. 11 is a top plan view of a portion of the inner cannula of the tissue cutting device of FIG. 1;

FIG. 12 is a top plan view of a portion of the outer cannula and inner cannula of FIG. 1 depicting the inner cannula inserted into the outer cannula;

FIG. 15 is an exploded assembly view of the tissue cutting device of FIG. 1;

FIG. 16a is a side elevation view of a cam of the tissue cutting device of FIG. 1;

FIG. 16b is an end elevation view of the cam of FIG. 16a;

FIG. 17a is a perspective view of a cam transfer mechanism of the tissue cutting device of FIG. 1;

FIG. 17b is a perspective view of a cam follower of the tissue cutting device of FIG. 1;

FIG. 28 is a side elevational view of the fluid supply sleeve of FIG. 1;

FIG. 29 is a partial close-up, longitudinal cross-sectional view of the fluid supply sleeve, outer cannula and inner cannula of FIG. 1;

FIG. 30 is a transverse cross-sectional view taken along line 30-30 in FIG. 29;

FIG. 31 is a close-up, partial side elevational view of the fluid supply sleeve of FIG. 1 selectively disposed along the length of the outer cannula of FIG. 1; and FIG. 32 is a close-up, partial top plan view of the fluid supply sleeve of FIG. 1 selectively disposed over a portion of the outer cannula opening of FIG. 1.

FIG. 33A is a partial cross-sectional view of a tissue collector with a chilling sleeve.

FIG. 33B is a partial cross-sectional view of a tissue collector with a normally closed cap member.

FIG. 33C is an end view of the normally closed cap member of FIG. 33B.

FIG. 33D is an enlarged view of an embodiment of the normally closed cap member of FIG. 33B.

DETAILED DESCRIPTION

Figure 4:
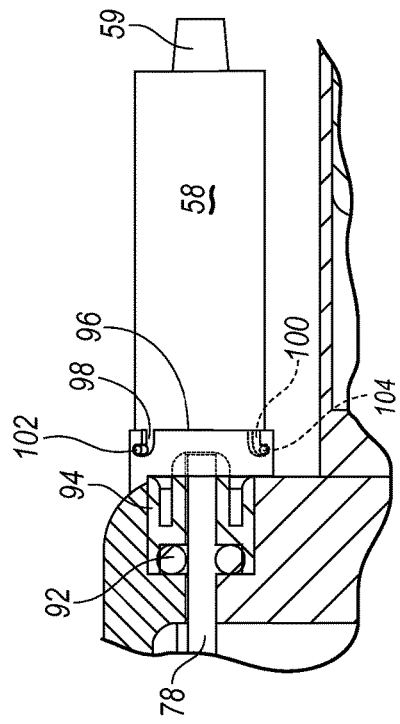
FIG. 4 is a partial cross-sectional view of the tissue cutting device of FIG. 1 in a first configuration in which a device-mounted tissue collector is disconnected from a tissue cutting device housing.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein are tissue cutting devices that are suited for surgical applications. While described herein in connection with neurosurgical applications such as the removal of spine and brain tissue, it is understood that the disclosure herein is applicable to other surgical applications and treatment protocols. As described herein, the devices may be configured with a fluid supply sleeve that may be selectively disposed on an outer cannula and selectively positionable along the length of the outer cannula. As a result, the fluid supply sleeve can be configured to supply fluids such as irrigants, hemostatic agents, pharmacological therapeutics and/or tissue sealants to a surgical site, and adjacent a tissue cutting opening of the surgical device 40. They can also be used to selectively adjust the area of the outer cannula aperture through which the aspiration is delivered through to the tissue.

Methods and system for preserving tissue samples for use in development of personalized medicine regimens are also disclosed. The systems disclosed herein permit transport of excised tissue samples, while protecting the tissue samples from, for example, adverse environmental stress.

Referring to FIG. 1, a tissue cutting device 40 includes a handpiece 42 and an outer cannula 44. In one exemplary embodiment, handpiece 42 is generally cylindrical in shape and is preferably sized and shaped to be grasped with a single hand. Handpiece 42 includes a lower housing 50 which comprises a proximal section 46 and distal section 48. Lower housing 50 comprises a proximal-most housing portion 82 (FIGS. 2 and 3) that is connected to a motor housing 71, and a cam housing 69 that is connected to motor housing 71. A front housing section 51 is connected to cam housing 69. Upper housing 52 is also provided. A tissue collector 58 may be operatively connected to upper housing 52 (as will be explained in further detail below). A rotation dial 60 for rotating the outer cannula 44 with respect to handpiece 42 is also mounted to upper housing 52.

Figure 20:
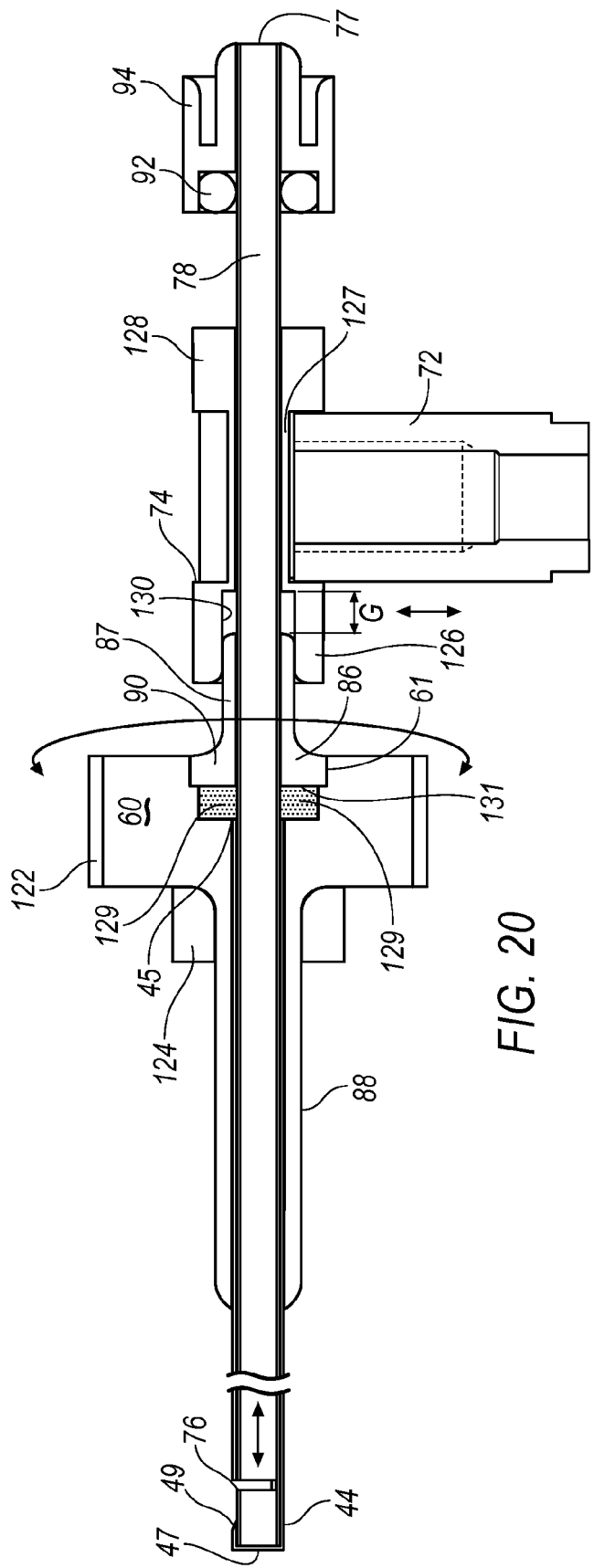
FIG. 20 is a side elevation view of an inner and outer cannula assembly of the tissue cutting device of FIG. 1.

As best seen in FIGS. 2, 3, and 20, outer cannula 44 includes an open proximal end 45, a closed distal end 47, and a distal opening 49 proximate distal end 47. Tissue cutting device 40 further comprises an inner cannula 76 which is partially disposed in an outer cannula lumen 110 (FIG. 8). Inner cannula 76 is configured to reciprocate within outer cannula lumen 110 and to cut tissue samples entering outer cannula 44 via outer cannula distal opening 49, without crush artifact or thermal damage, as will be described in greater detail below. Inner cannula 76 reciprocates between a proximal position, which is depicted in FIG. 2 and a distal position which is depicted in FIG. 3. Inner cannula 76 includes an open proximal end 77 and an open distal end 79. Distal end 79 is configured to cut tissue, and in exemplary embodiments is capable of cutting neurological system tissues such as those from the brain or spine. In one exemplary embodiment, inner cannula distal end 79 is beveled in a radially inward direction to create a sharp circular tip and facilitate tissue cutting.

Outer cannula 44 is not translatable with respect to handpiece 42 such that its position with respect to handpiece 42 along the direction of the longitudinal axis of handpiece 42 remains fixed. An exemplary fluid supply sleeve 302 (FIG. 1) may be selectively attachable to outer cannula 44. Fluid supply sleeve 302 is configured to allow fluids to be provided proximate a surgical site and/or adjacent distal opening 49. In one exemplary configuration, fluid supply sleeve 302 has a proximal hub 306 and a distal end 320. An outer cannula opening 322 is provided at the proximal end of fluid supply sleeve 302. An elongated channel section 304 is connected to proximal hub 306 and projects distally away from it. Distal end 320 of fluid supply sleeve 302 is the distal end of the elongated channel section 304. In FIG. 1, fluid supply sleeve 302 is shown in an installed condition on outer cannula 44. In the depicted installed condition, fluid supply sleeve 302 is selectively positionable along the length of outer cannula 44.

In FIGS. 2-3, fluid supply sleeve 302 is not shown for ease of viewing. Motor 62 is disposed in proximal lower housing section 46 of handpiece 42 and is operably connected to inner cannula 76 to drive the reciprocation of inner cannula 76 within outer cannula lumen 110. Motor 62 may be a reciprocating or rotary motor. In addition, it may be electric or hydraulic. However, in the embodiment of FIGS. 2 and 3, motor 62 is a rotary motor, the rotation of which causes inner cannula 76 to reciprocate within outer cannula lumen 110.

Motor 62 is housed in motor housing 71, which defines a portion of lower housing proximal section 46. Motor 62 is connected to an inner cannula drive assembly 63 which is used to convert the rotational motion of motor 62 into the translational motion of inner cannula 76. At its proximal end, motor housing 71 is connected to proximal-most housing portion 82, which includes a power cable port 84 and a hose connector 43, which in the exemplary embodiment of FIG. 3 is configured as an eyelet. However, it is understood that hose connected 43 may embody other configurations. Hose connector 43 provides a mechanism for securely retaining a vacuum system hose to handpiece 42, thereby allowing vacuum to be supplied to tissue collector 58.

Inner cannula driver assembly 63 (not separately shown in figures) comprises a cam 64, a cam follower 68, a cam transfer 72, and a cannula transfer 74. Cam 64 is a generally cylindrical structure and is shown in detail in FIGS. 16A and 16B. A groove or channel 65 is defined in the surface of cam 64. In one exemplary embodiment, groove 65 is continuous and circumscribes the perimeter of cam 64 but is not oriented perpendicularly to the longitudinal axis of cam 64, i.e., groove 65 is angled with respect to the cam axis. Opposing points on groove 65 such as points 65a and 65b (FIGS. 2 and 3) define pairs of "apexes" that are spaced apart along the longitudinal axis of the cam, i.e., the groove extends along a portion of the length of the cam. Cam 64 also includes a proximal opening 114 (FIG. 16a) for receiving a motor shaft and a proximal recess 116 into which a shaft may be snugly received. Holes 118 and 120 are provided for mounting position indicators that cooperate with a position sensor to determine the angular position of cam 64, and correspondingly, the linear position of inner cannula 76 within the outer cannula lumen 110, as discussed below.

Cam follower 68 is depicted in detail in FIG. 17B. Cam follower 68 is a generally rectangular block shaped structure with a hollow interior in which cam 64 is partially disposed. Cam follower 68 also includes a hole 70 in its upper face in which a ball bearing (not shown) is seated. The ball bearing rides in cam groove 65 and engages cam transfer 72. As a result, when cam 64 rotates, cam follower 68 translates along the length of handpiece 42. Cam follower 68 also includes lateral slots 182a and 182b that cooperatively engage corresponding members 178a, 178b from cam transfer 72.

Cam follower 68 is disposed within a cam chamber 67 formed in cam housing 69. Cam 64 is partially disposed in cam chamber 67 and extends proximally therefrom to engage motor 62. Cam housing 69 comprises part of distal portion 48 of handpiece 42. Cam 64 does not reciprocate within cam chamber 67 and instead merely rotates about its own longitudinal axis. However, cam follower 68 reciprocates within cam chamber 67 along the direction of the length of handpiece 42. Cam follower 68 is open at its proximal end to receive cam 64. As shown in FIGS. 15 and 16A, cam 64 may optionally include a threaded distal end 123 that projects through a distal opening 191 (FIG. 17b) in cam follower 68 and which engages a nut 190 (FIG. 15) to prevent reciprocation of cam 64 relative to cam housing 69. Proximal cam bearing 186 and distal cam bearing 188 (FIG. 15) may also be provided to support cam 64 as it rotates within cam housing 69.

Cam transfer 72 extends from cam chamber 67 into a cam transfer chamber 73 formed in upper housing 52. As best seen in FIG. 17a, cam transfer 72 comprises a proximal end 72a that is attachable to cam follower 68 and a distal end 72b that is attachable to inner cannula 76 via cannula transfer 74. Proximal end 72a comprises a pair of spaced apart, downwardly extending members 178a and 178b, and distal end 72b comprises a pair of spaced apart upwardly extending members 180a and 180b. Downwardly extending members 178a and 178b are spaced apart in a direction that is perpendicular to the length of cam 64 and handpiece 42, while upwardly extending members 180a and 180b are spaced apart in a direction that is parallel to the length of cam 64 and handpiece 42. Cam follower slots 182a and 182b engage downwardly extending members 178a and 178b of cam transfer 72. Downwardly extending members 178a and 178b of cam transfer 72 may be resilient and may have engagement portions 179a and 179b on their free ends (e.g., hooks or clips) for securely engaging the bottom and side surfaces of cam follower 68.

As best seen in FIG. 20, cannula transfer 74 comprises a sleeve disposed about inner cannula 76. For ease of viewing, fluid supply sleeve 302 is not shown in FIG. 20. Cannula transfer 74 comprises a proximal end 128, middle section 127, and distal end 126. Upwardly extending members 180a and 180b of cam transfer 72 define fork-shaped structures that receive and cradle middle section 127 of cannula transfer 74. Distal end 126 and proximal end 128 of cannula transfer 74 are disposed outwardly of upwardly extending members 180a and 180b and are shaped to prevent relative translation between cam transfer 72 and cannula transfer 74. In the depicted embodiments, distal end 126 and proximal end 128 of cannula transfer 74 are enlarged relative to middle section 127 to abut the upwardly extending, fork-shaped members 182a and 182b, thereby preventing relative translation between cam transfer 72 and cannula transfer 74. As a result, when cam transfer 72 reciprocates along the length of handpiece 42, cannula transfer 74 reciprocates as well. Because it is affixed to inner cannula 76, when cannula transfer 74 reciprocates, it causes inner cannula 76 to reciprocate within outer cannula 44.

In one exemplary arrangement, motor 62 is a brushed DC motor and may be operably connected to cam 64 in a number of ways. In the embodiment of FIGS. 2 and 3, motor 62 includes a distally extending shaft 66 that extends into a proximal opening 114 and engages recess 116 (FIGS. 16A and B) defined in cam 64. Shaft 66 may be connected to cam 64 via a threaded connection, adhesive, or other known connection means. In an alternate implementation, depicted in FIG. 15, a separate cam coupler 184 is provided. Cam coupler 184 is seated in proximal opening 114 and has a width greater than the diameter of opening 114. Cam coupler 184 is also connected to motor shaft 66 such that rotation of shaft 66 causes cam coupler 184 to rotate, which in turn causes cam 64 to rotate therewith. One revolution of motor shaft 66 causes cam 64 to rotate by one revolution, which in turn causes inner cannula 76 to reciprocate by one complete stroke, i.e., from the position of FIG. 2 to the position of FIG. 3 and back to the position of FIG. 2.

Cam transfer 72 may be connected to cam follower 68 by mechanical means, adhesive means or other known connection means. In one exemplary embodiment, downwardly extending members 178a and 178b mechanically clip onto and removably engage cam follower 68. In another embodiment, cam transfer 72 is adhesively affixed to cam follower 68. In yet another embodiment, both mechanical and adhesive connections are used. The ball bearing (not shown) disposed in cam follower hole 70 traverses cam groove 65 as cam 64 rotates, causing cam follower 68 to reciprocate from the proximal position of FIG. 2 to the distal position of FIG. 3. As a result, cam transfer 72, cannula transfer 74 and inner cannula 76 translate between their respective proximal positions of FIG. 2 and their respective distal positions of FIG. 3 when motor 62 and cam 64 rotate.

Figure 14:
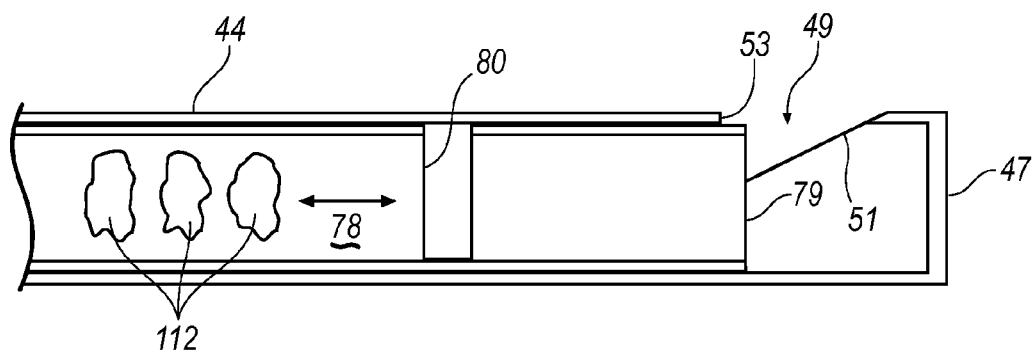
FIG. 14 is a partial cross-sectional view of a distal region of the outer cannula and the inner cannula of the tissue cutting device of FIG. 1, depicting the inner cannula in a second relative position with respect to the outer cannula.

Motor 62 is preferably selected to have a rotational speed that allows inner cannula 76 to reciprocate from the position of FIG. 2 to the position of FIG. 3 and back to the position of FIG. 2 at a rate of at least about 1,000 reciprocations/minute. Reciprocation rates of at least about 1,200 reciprocations/minute are more preferred, and reciprocation rates of at least about 1,500 reciprocations/minute are even more preferred. Reciprocation rates of less than about 2,500 reciprocations/minute are preferred. Reciprocation rates of less than about 2,000 are more preferred, and reciprocation rates of less than about 1,800 reciprocations/minute are even more preferred. As best seen in FIG. 14, the rates of reciprocation of device 40 allow tissue to be severed into "snippets" 112 which are relatively smaller than "slug" tissue samples obtained by many prior devices. The smaller sized "snippet" 112 format permits use of the excised tissue samples for pathology or diagnostic purposes without necessarily requiring further manual or mechanical reduction of sample sizes. The smaller size samples provides a benefit as handling of tissue samples to reduce the size of excised tissue samples may expose the tissue to environmental factors that may degrade or otherwise compromise the biological integrity of the tissue samples. For example, in reducing the size of the excised tissue samples, bacteria may be inadvertently introduced. In the exemplary configuration shown, as the reciprocation of the tissue cutting device continues, a continuum of severed tissue snippets 112 is obtained.

As mentioned previously, outer cannula 44 includes an opening 49 for receiving tissue into outer cannula lumen 110. As best seen in FIGS. 8-12, opening 49 is preferably defined by a cutting edge 51 that is configured to sever tissue and a non-cutting edge 53 that is not configured to sever tissue. In certain exemplary implementations, cutting edge 53 has a radial depth "d" that is no greater than about 50% of the outer diameter of outer cannula 44. In one exemplary implementation, cutting edge 51 is beveled in a radially inward direction, non-cutting edge 53 is not beveled, and cutting edge 51 is located immediately distally of non-cutting edge 53. Inner cannula distal end 79 is preferably configured to cut tissue. In one exemplary embodiment, distal end 79 is beveled in a radially inward direction around the circumference of inner cannula 76 to provide a sharp edge. As tissue is received in outer cannula opening 49, it is compressed between inner cannula distal end 79 and outer cannula cutting edge 51, causing the received tissue to be cleanly severed from the surrounding tissue, without crush artifact or thermal damage to the tissue.

Tissue cutting device 40 is particularly well suited for use in cutting tough tissues such as spinal and brain tissues. Outer cannula 44 and inner cannula 76 comprise materials that are generally rigid, such as rigid plastics or metal. In one preferred implementation, both cannulae comprise stainless steel, and more preferably, 304SS typically used in medical grade instruments.

As best seen in FIGS. 9-14, to facilitate the cutting of tough tissues, inner cannula 76 includes a hinge 80. For ease of viewing, fluid supply sleeve 302 is not shown in FIGS. 9-14. Hinge 80 is located between inner cannula body section 81 which is located on the proximal side of hinge 80 and inner cannula cutting section 83 which is located on the distal side of hinge 80. In one exemplary arrangement, hinge 80 is a living hinge. As used herein, the term "living hinge" refers to a thin, flexible hinge that joins two relatively more rigid parts together. In one example, hinge 80 is a living hinge that is integrally formed with inner cannula body section 81 and inner cannula cutting section 83 by removing a portion of the circumference of the inner cannula 76 along a length L (FIG. 11). Hinge 80 allows cutting section 83 to pivot about hinge 80 as inner cannula 76 reciprocates within outer cannula 44. As inner cannula 76 translates in the distal direction, it contacts tissue received in outer cannula opening 49 and encounters progressively increasing resistance from the tissue as the tissue is urged in the distal direction. As the resisting force of the tissue increases, cutting section 83 pivots progressively more until a zero annular clearance is obtained between inner cannula distal end 79 and outer cannula opening 49. The received tissue is severed and aspirated in the proximal direction along inner cannula lumen 78 and received in tissue collector 58. Thus, inner cannula lumen 78 provides an aspiration path from the inner cannula distal end 79 to the inner cannula proximal end 77. Hinge 80 allows a generally zero annular clearance to be obtained between inner cannula distal end 79 and outer cannula opening 49 at cutting section 83 while not affecting the annular clearance between inner cannula body section 81 and outer cannula 44. This configuration maximizes tissue cutting while minimizing frictional losses that would otherwise occur due to the frictional engagement of the outer surface of inner cannula body section 81 and the inner surface of outer cannula 44 if a very small annular clearance between the outer cannula 44 and inner cannula 76 were present.

Outer cannula opening 49 may have a number of shapes. In certain examples, when outer cannula opening 49 is viewed in plan, it has a shape that is generally square, rectangular, trapezoidal, ovular, or in the shape of the letter "D." In certain other exemplary implementations, outer cannula opening 49 is configured to direct tissue so that it may be compressed as inner cannula 76 translates in the distal direction. In one exemplary embodiment, depicted in FIGS. 10 and 12, outer cannula opening 49 has a generally triangular shape when outer cannula opening 49 is viewed in plan. As FIGS. 10 and 12 indicate, when viewed in plan, the width of opening 49 in a direction transverse to the outer cannula longitudinal axis varies longitudinally along the length of outer cannula 44, and preferably narrows from the proximal to distal portions of opening 49. When viewed in side elevation, cutting edge 51 slopes in a radially outward direction moving distally along edge 51. As a result, as a tissue sample is distally urged within outer cannula opening 49 by the action of inner cannula 76, the tissue is increasingly compressed in the direction of the circumference of inner cannula 76 (or in the direction of the "width" of opening 49 when viewed in plan). To ensure complete cutting, inner cannula distal end 79 preferably travels to a position that is distal of outer cannula opening 49 during a tissue cutting operation, i.e., there is an inner cannula overstroke.

Figure 21A:
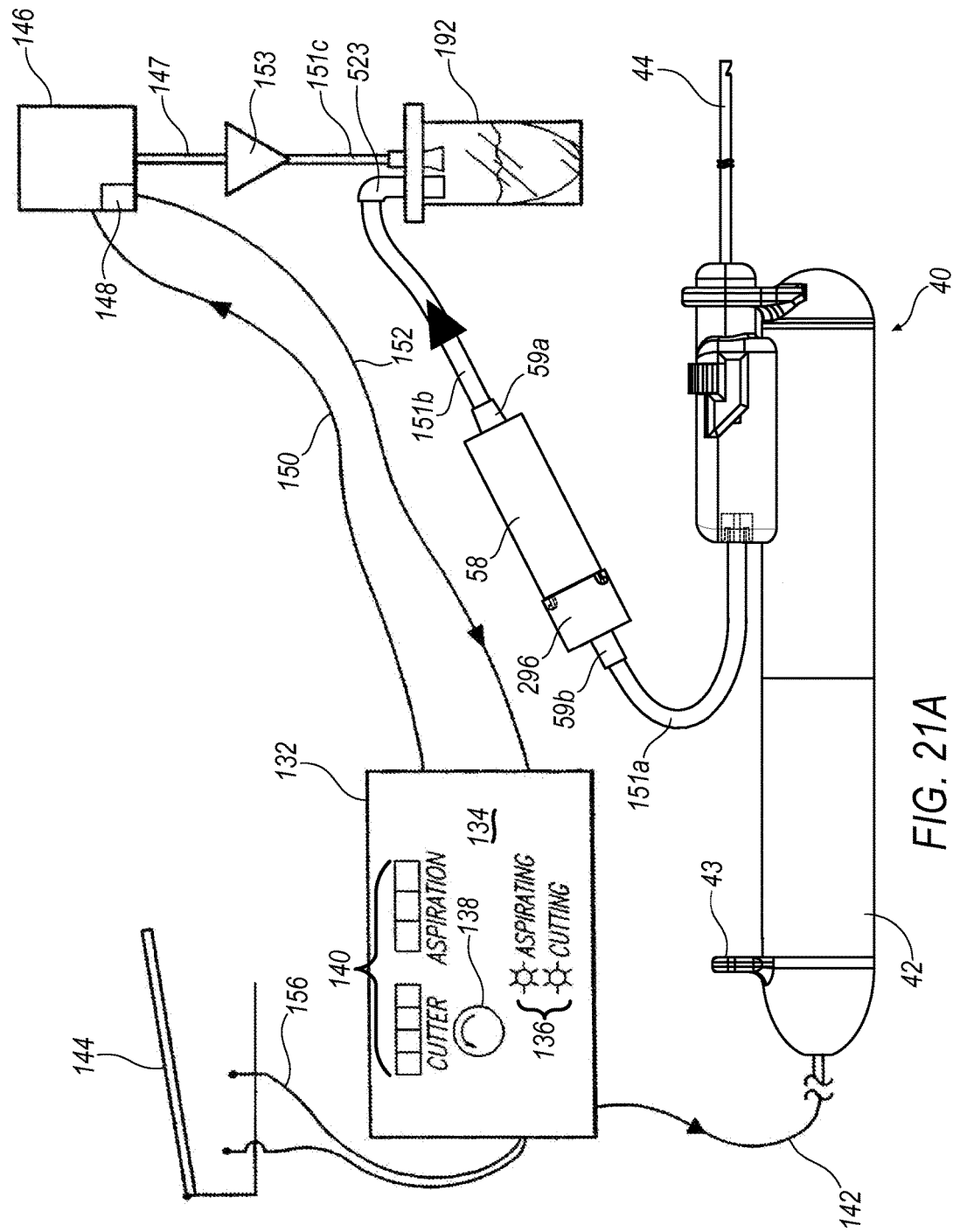
FIG. 21A is a tissue cutting system including a remote tissue collector, control console, foot pedal, and the tissue cutting device of FIG. 1.

As mentioned above, tissue cutting device 40 aspirates tissue samples received in inner cannula lumen 78 to cause the tissue samples to move in the proximal direction along the length of the inner cannula 76. In embodiments wherein tissue collection is desired, device 40 preferably includes a tissue collector 58 into which aspirated tissue samples are deposited during a tissue cutting procedure. Tissue collector 58 may be located remotely from handpiece 42 and outside the sterile field during a tissue cutting operation as shown in FIG. 21A. However, in certain embodiments, as best seen in the examples of FIGS. 1-7, tissue collector 58 is removably connected directly to handpiece 42 within the sterile field. However, it is understood that tissue collector 58 may also be remotely connected to handpiece 42, while in the sterile field, as well. In either embodiment, a fluid collection canister 192 may be located between tissue collector 58 and a source of vacuum (such as vacuum generator 153 in FIG. 21A) to protect the vacuum generating apparatus from becoming contaminated or damaged by aspirated fluids.

In other embodiments, a tissue collector may be omitted and fluid collection canister 192 may be provided to collect both aspirated fluid and tissue. Further, fluid collection canister 192 may also be provided with a tissue preservation solution configured to maintain the tissue samples viability and biological integrity, such as, for example, a nutrient rich solution designed to maintain the tissue samples in an aseptic environment.

Referring to FIGS. 4-7, tissue collector 58 is connected to upper housing 52 proximally of the inner cannula 76 to receive the aspirated tissue samples. Tissue collector 58 is a generally cylindrical, hollow body with an interior volume that is in fluid communication with the inner cannula lumen 78 and a source of vacuum (not shown in FIGS. 4-7). Tissue collector 58 may be removably secured to housing connector 96 to allow for the periodic removal of collected tissue samples, including while in the sterile field. Tissue collector 58 is preferably secured to upper housing 52 in a manner that provides a substantially leak-proof vacuum seal to maintain consistent aspiration of severed tissue samples. A vacuum hose fitting 59 is formed on the proximal end of tissue collector 58 and is in fluid communication with the interior of tissue collector 58 and with a vacuum generator, as will be discussed below.

To enable the severed tissue samples to be used for personalized medicine regimens, viability and integrity of the tissue samples must be maintained after removal of the tissue samples from the patient, and during the collection and transport of the tissue samples to the oncological laboratory. More specifically, the tissue samples must be kept biologically active and intact, while maintained in a sterile or aseptic environment to permit the tissue to be cultured. Further, physiologic stress on the tissue samples must be minimized so as not to adversely impact the samples.

Referring to FIG. 33A, to assist in maintaining the viability and integrity of the tissue samples, in one exemplary arrangement, tissue collector 58 is provided with a cooling sleeve 400 that surrounds a portion of an outer surface of tissue collector 58. Cooling sleeve 400 is configured to keep tissue collector 58 at a predetermined cool temperature range which is sufficient to maintain viability of the tissue samples captured within tissue collector 58 and at least combat physiological stress and degradation of the tissue samples due to temperature. In one exemplary configuration, cooling sleeve 400 is configured with a body portion 404 that generally corresponds to the outer contour of tissue collector 58, i.e., generally in the shape of a tube. Alternatively, cooling sleeve 400 may be provided as a flexible sheet that may be wrapped around an outer surface of tissue collector 58, with suitable securing features (such as hook and loop fasteners) being utilized to secure cooling sleeve to tissue collector 58. In either arrangement, body portion 404 is sized to receive tissue collector 58 therein and extends about at least a great portion of the length of tissue filter 58. An optional substantially closed end face 402 may be provided that further includes an opening 406 that is configured to permit vacuum hose fitting 59 to exit cooling sleeve 400. However, it is understood that because tissue collector 58 maintains a sterile/aseptic environment for the tissue contents inside tissue collector 58, cooling is not necessarily required to be provided as a sterile component of the system. This configuration thus allows for flexibility in the applicability and ease of use of the cooling sleeve.

In one exemplary configuration, cooling sleeve 400 may include electrically powered cooling elements (not shown), that are operatively connected to a power source. When activated, cooling sleeve 400 keeps tissue samples captured within tissue collector 58 at a stable, preselected temperature during collection, while cooling sleeve 400 is operatively positioned around tissue collector 58.

In another exemplary configuration, cooling sleeve 400 may be configured similar to an ice pack, in that the sleeve is configured with water, refrigerant gel or liquid sealed within between the layers of the material. In this arrangement, cooling sleeve 400 may be simply stored in a freezer until a surgical procedure and then positioned on tissue collector 58. Further, because there is no need for an electrical power source, cooling sleeve 400 may be used to control temperature during collection and through transport to the oncological lab. To maintain the proper shape for cooling sleeve 400, a shaper that generally corresponds to the shape of the tissue collector may be provided that is inserted into cooling sleeve 400, while cooling sleeve 400 is stored in a freezer.

Figure 21B:
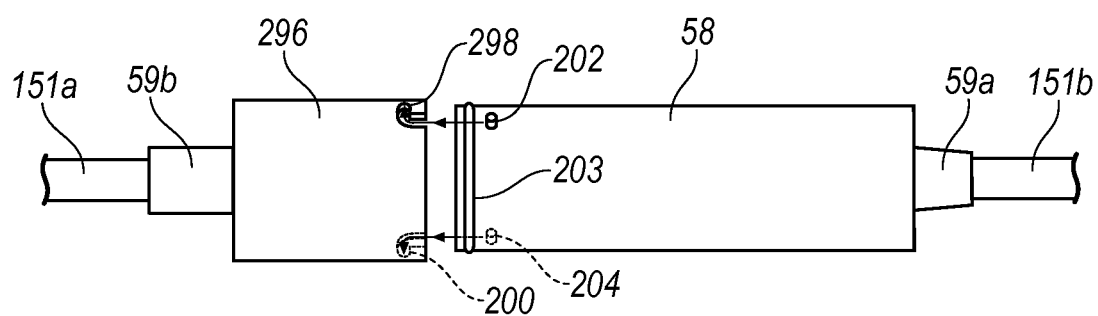
FIG. 21B is an enlarged view of the remote tissue collector of FIG. 21A.
Figure 21C:
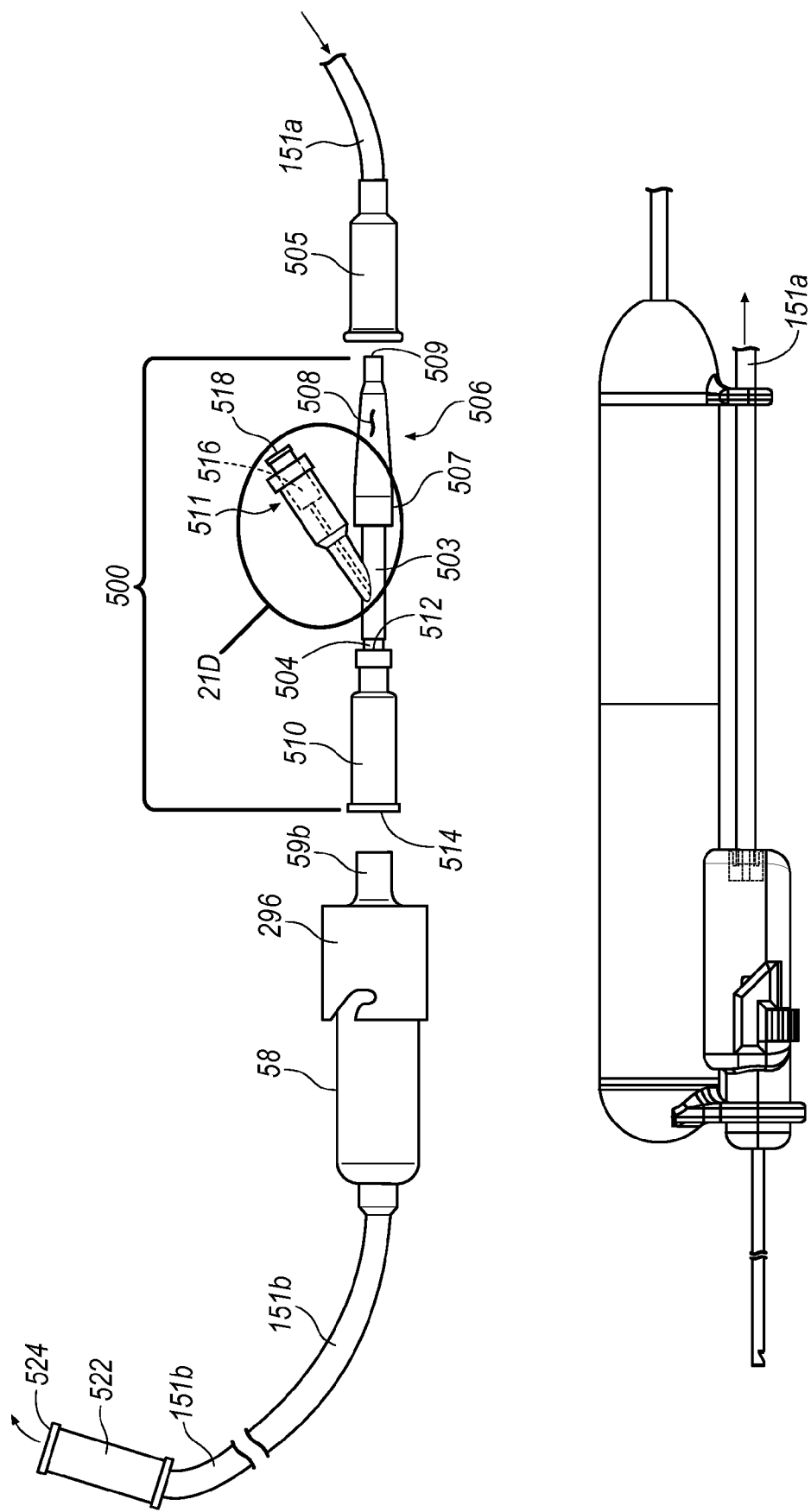
FIG. 21C is an embodiment of a part of the tissue cutting system of FIG. 21A, with a tissue preservation adapter system positioned between the tissue collector and the tissue cutting device.

Another exemplary embodiment of a cooling system 600 is shown in FIGS. 34-37. Cooling system 600 is utilized in those embodiments where tissue collector 58 is remotely connected to tissue resection device 40, as shown in FIGS. 21A-C, for example. Cooling system 600 includes a base member 602 and a lid 604. Base member 602 is configured as an insulated member that comprises a reservoir 606 and a tissue collector chamber 608. In one exemplary arrangement, tissue collector chamber 608 is defined by a contoured wall 610, integral with base member 602. However, it is understood that a separate sleeve member may be positioned within base member 602 to serve as a tissue collector chamber 608.

In one exemplary arrangement, a sleeve member 612 lines and is in contact with the outside of tissue collector chamber 608. Sleeve member 612 is constructed of a thermally conductive material, as will be explained in further detail below. The wall member that defines tissue collector chamber 608 further comprises an opening 614 (best shown in FIG. 36) that is in communication with reservoir 606. As will be explained further below, opening 614 also permits sleeve member 612 to directly contact any material that is contained within reservoir 606.

Base member 602 further comprises a narrow slit 616. Slit 616 extends from a top edge 618 of base member 602 to a bottom of tissue collector chamber 608. Slit 616 is sized to permit vacuum line 151b to pass through.

Lid 604 is sized to fit over base member 602 to retain materials positioned within reservoir 606, as well as to retain tissue collector 58 therein. Lid 604 further includes an opening 619 through which hose fitting 59b extends, when tissue collector 58 is positioned within tissue collection chamber 608. In one embodiment, a bottom surface 620 of lip 604 is provided with a projecting element 622 configured to fit within an opening of reservoir 606. A seal member (not shown) may be provided around a peripheral edge 624 of projecting element 622 to provide a water tight/sealed chamber. An external latching member may be provided to secure lid 604 to base member 602.

In operation, lid 604 is removed from base member 602. Reservoir 606 is filled with a suitable refrigerant (i.e., ice or other suitable liquid). Tissue collector 58 is positioned within tissue collector chamber 608, with vacuum line 151b extending out of slit 616. Lid 604 is then attached to base member 602, sealing reservoir 606. Hose fitting 59b extends upwardly from lid 604 and is connected via vacuum line 151a to tissue resection device 40.

Due to the thermo-conductivity of sleeve 612, and because sleeve 612 is in direct communication with the refrigerant positioned within reservoir 606, tissue collector 58 (and hence any tissue samples positioned therein) are kept at a suitable temperature to maintain tissue viability. Moreover, since reservoir 606 for the refrigerant is insulated and water tight, ice or liquid refrigerants may be directly placed into reservoir 606 and replenished as necessary during use. Further, in another exemplary configuration, base member 602 may be provided with an external temperature gauge 626. Temperature gauge 626 is configured to be in communication with reservoir 606 or in communication with sleeve 612 thereby providing an indication when additional refrigerant may be needed and of the thermal status of the contents within tissue collector 58. For example, in one exemplary configuration an end portion of sleeve 612 is extended along a portion of base member 602. An opening (not shown) is provided through a surface of base member 602 and temperature gauge 626 is positioned over the opening and in contact with the extended portion of sleeve 612. Accordingly, the temperature of tissue collector 58 is communicated to temperature gauge 626.

In another exemplary arrangement, an opening (not shown) is formed in the inside surface of base member 602, similar to opening 614. Temperature gauge 626 is positioned within base member 602 over the opening so as to be effectively in contact with reservoir 606.

Further, in addition to slit 616 providing an exit path for vacuum line 151*b*, slit 616 also provides an additional function. More specifically slit 616 permits viewing of the tissue collector 58, which is preferably constructed of transparent or translucent material, while positioned within cooling system 600. With this configuration, a user will be able to determine when tissue collector 58 is full of tissue samples.

When tissue collection is complete, vacuum line 151*b* may be disconnected from hose fitting 59*b* and vacuum line 151*a* may be disconnected from tissue resection device 40, while leaving tissue collector 58 within cooling system 600, thereby maintaining the tissue samples in a sterile/aseptic environment, at an appropriate temperature.

To assist in removing tissue samples from tissue collector 58, in some embodiments, a selectively removable tissue filter 405 may be positioned within tissue collector 58. Tissue filter 405 may be configured with a mesh body that retains tissue samples there within, but permits bodily fluids to exit through the mesh body. In operation, upon completion of tissue resection, tissue collector 58 is detached from housing connector 98 and tissue filter 405, holding tissue samples therein, may be removed from tissue collector 58. In some arrangements, tissue samples will be removed from tissue filter 405, while in the operating room and placed in a suitable container for transport (to be explained in further detail below). To assist in removal of tissue samples from tissue filter 405, in one exemplary arrangement, tissue filter 405 is configured with scoop 407 that is disposed within tissue filter 405. Scoop 407 includes an end portion 409 that is configured to be approximately the same size and shape as the interior of tissue filter 405. End portion 409 is secured to a pull member 410 that loops around an outer surface of tissue filter 405. To remove tissue samples from filter 405, pull member 410 is pulled away from tissue filter 405, which causes scoop 407 to advance tissue samples to the opening of tissue filter 405. In another exemplary configuration, tissue filter 405 may be configured with a hinge member as shown and described in U.S. Pat. No. 7,556,622, the contents of which are incorporated herein by reference.

In some instances, it may be desirable to transport tissue collector 58 with tissue samples still collected therein, to the oncological lab. For example, to maintain the temperature of the tissue samples during transport, tissue collection 58, with cooling sleeve 400 still in place may be transported to the oncological lab. However, for embodiments where the tissue collector 58 is directly connected to the device 40, such as that shown in FIGS. 1-7, the distal end of tissue collector 58 is typically configured to be generally open. Because it is contemplated that tissue collector 58 would be removed from surgical device 40 once tissue resection is complete, in one exemplary configuration, tissue collector 58 may be provided with a normally closed, and selectively removable sterile cap member 408, shown in FIGS. 33B-33C to assist in retaining samples within tissue collector 58 during transport. In one exemplary configuration, cap member 408 is constructed of a resilient material that frictionally grips an outer edge of the distal end of tissue collector 58. A normally closed opening 412, such as a slit, serves to retain the tissue samples within tissue collector 58, when vacuum is turned off and when tissue collector 58 is removed from device 40. However, in operation, inner cannula proximal end 77 will force opening 412 to permit tissue samples to enter into tissue collector 58. Once tissue collector 58 is transported to its destination, cap member 408 may be removed from the distal end of tissue collector 58, and the tissue samples may be released. In another exemplary configuration, shown in FIG. 33D, cap member 408 is provided with an extended sleeve 414 into which distal end of tissue collector 58 is received. Sleeve 414 may be configured to be selectively perforated, ruptured or torn, to release sleeve 414 from tissue collector 58. In one exemplary arrangement, a tab member 416 may be provided to facilitate the release of sleeve 414 from tissue collector 58.

Figure 5:
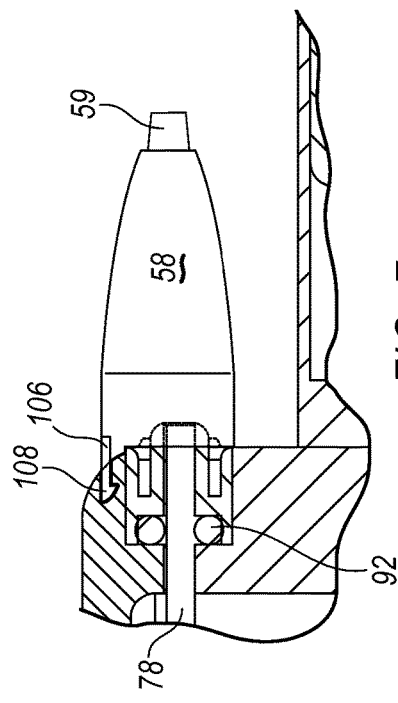
FIG. 5 is a partial cross-sectional view of the tissue cutting device of FIG. 4 in a second configuration in which the device-mounted tissue collector is connected to the tissue cutting device housing.

In the embodiment of FIGS. 4-5, housing connector 96 is a generally cylindrical, flange extending proximally from upper housing 52. Upper shell 54 and lower shell 56 of upper housing 52 cooperatively define a cavity into which a seal holder 94 is partially disposed. Seal holder 94 includes a distal annular recess in which a seal 92, such as an o-ring, is disposed. Seal holder 94 also includes a central lumen through which inner cannula 76 is slidably disposed. A proximally projecting portion 95 of seal holder 94 projects away from upper housing 52 in the proximal direction and is received within housing connector 96. As best seen in FIGS. 2 and 3, inner cannula proximal end 77 preferably remains within seal holder 94 as inner cannula 76 reciprocates during operation of tissue cutting device 40. However, proximal end 77 moves within seal holder 94 as inner cannula 76 reciprocates. Seal 92 preferably comprises a resilient material such as an elastomeric material. The sealing engagement of seal 92 and inner cannula 76 prevents air or fluids from leaking between inner cannula 76 and upper housing 52 and aids in maintaining consistent aspiration of samples through the inner cannula lumen 78.

Housing connector 96 includes connecting features 98 and 100 which are configured to engage with corresponding connecting features 102 and 104 on tissue collector 58. In the embodiment of FIGS. 4 and 5, connecting features 98 and 100 are "J" shaped slots formed in housing connector 96, and connecting features 102 and 104 are complementary protrusions formed on tissue collector 58 which engage connecting features 98 and 100, respectively. To connect tissue collector 58 to housing connector 96, protrusions 102 and 104 are aligned with slots 98 and 100, and tissue collector 58 is then inserted into housing connector 96 in the distal direction. Tissue collector 58 is then rotated to fully engage protrusions 102 and 104 with slots 98 and 100. A seal 103 is provided around the circumference of tissue collector 58 to sealingly engage the inner surface of housing connector 96.

Figure 6:
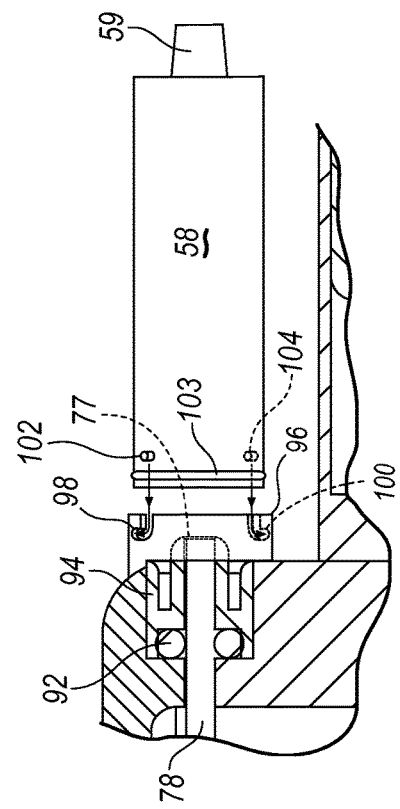
FIG. 6 is a partial cross-sectional view of an alternate embodiment of the tissue cutting device of FIG. 1 in a first configuration in which the device-mounted collector is disconnected from the tissue cutting device.
Figure 7:
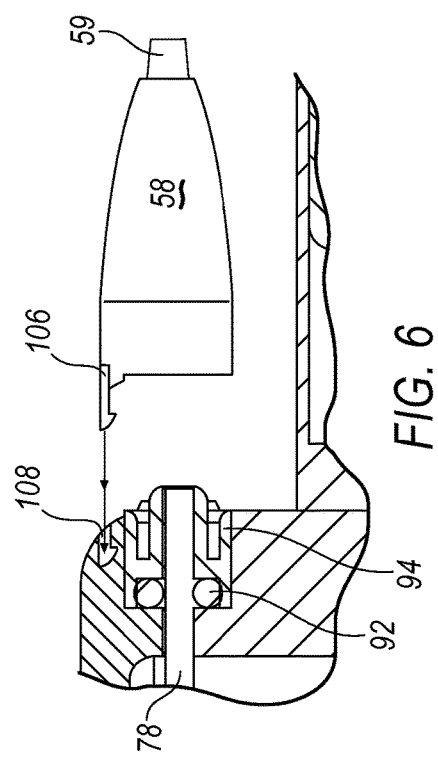
FIG. 7 is partial cross-sectional view of the tissue cutting device of FIG. 6 in a second configuration in which the device-mounted tissue collector is connected to the tissue cutting device.
Figure 13:
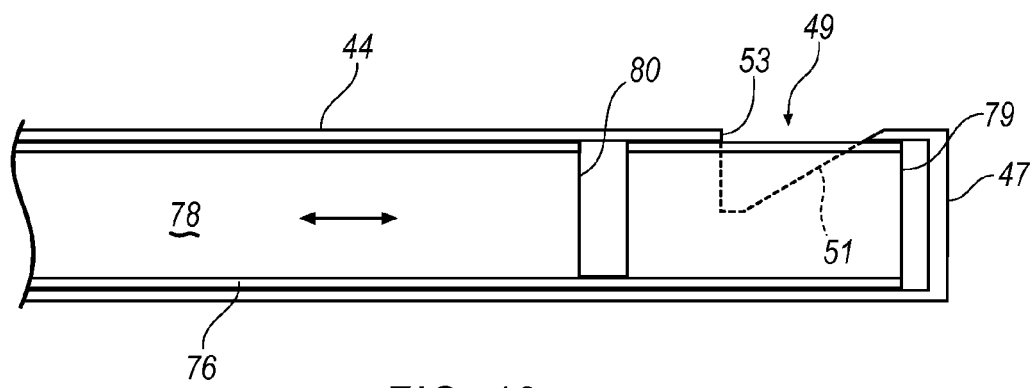
FIG. 13 is a partial cross-sectional view of a distal region of the outer cannula and the inner cannula of the tissue cutting device of FIG. 1, depicting the inner cannula in a first relative position with respect to the outer cannula.

An alternate embodiment of tissue collector 58 is depicted in FIGS. 6 and 7. In the embodiment of FIGS. 6 and 7, tissue collector 58 is semi-elliptical in cross-section and includes a hollow interior for receiving samples, as in the embodiment of FIGS. 4 and 5. In the embodiment of FIGS. 6 and 7, a cylindrical flange housing connector 96 is not provided. Instead, upper housing 52 is formed with an engagement recess 108 that engages a complementary clip 106 formed on tissue collector 58. In each of the foregoing embodiments, tissue collector 58 may be provided with a filter (as described above) in its interior for collecting solid tissue samples while allowing liquids and gases (e.g., air) to pass through. Exemplary filters include medical grade mesh filters with a mesh size smaller than that of tissue snippets 112. Further, while not specifically shown, it is understood that tissue collector 58 shown in FIGS. 6-7 may also be provided with a cooling sleeve, as described above.

In the embodiments of FIGS. 4-7, tissue collector 58 preferably has a longitudinal axis that is not collinear with the longitudinal axes of handpiece 42, motor 62, or cam 64. The longitudinal axis of tissue collector 58 may be arranged so as to be substantially coaxial with the longitudinal axis of inner cannula 76 to yield an "in-line" filter configuration. Tissue collector 58 and inner cannula 76 are both spaced apart from and substantially parallel to the longitudinal axes of handpiece 42, motor 62, and cam 64. Thus, the cutting axis (i.e., the outer cannula longitudinal axis) and sample aspiration path axis are not coaxial with the longitudinal axis of the handpiece 42. As a result, when device 40 is used to cut tissue, the surgeon's view of the cutting axis is not obstructed by his or her hand. In addition, the surgeon can treat the proximal end of the filter as a "gun sight" and align it with a tissue sample to be cut to thereby align the outer cannula 44 with the tissue sample, providing enhanced ergonomic benefits over previous devices, in particular, previous neurosurgical devices. In the case of a device with a remote tissue collector 58 such as the one depicted in FIGS. 21A-21C, the user can treat the proximal end of upper housing 52 as a gun sight and align it with a target tissue.

Figure 18:
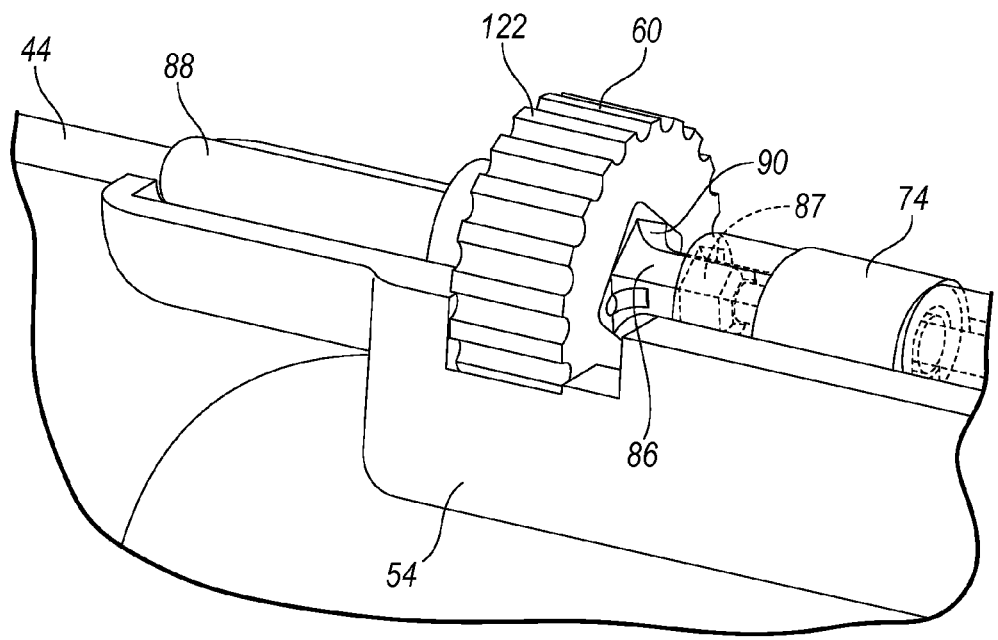
FIG. 18 is a partial perspective view of a portion of the tissue cutting device of FIG. 1 with an upper shell of an outer sleeve upper housing removed to show a dial for rotating an outer cannula.
Figure 19:
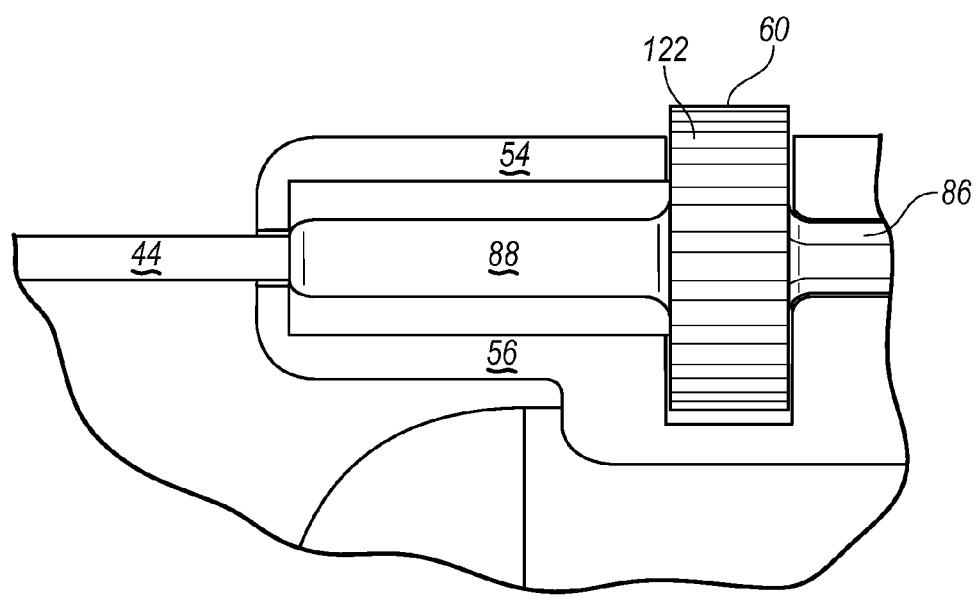
FIG. 19 is a partial side cross-sectional view of the portion of the tissue cutting device of FIG. 18.

When device 40 is used to cut tissue, outer cannula opening 49 must be aligned with the target tissue of interest to receive it for cutting. The entire device 40 can be rotated about the longitudinal axis of handpiece 42 to place outer cannula opening 49 at the desired location. However, this technique can be awkward and may reduce the surgeon's dexterity. Thus, in an exemplary embodiment, device 40 includes a selectively rotatable outer cannula 44. As best seen in FIGS. 18-20, a rotation dial 60 is provided and is rotatably seated in a cavity defined by upper shell 54 and lower shell 56 of upper housing 52. Rotation dial 60 is configured such that when it is rotated, it causes outer cannula 44 to rotate about its longitudinal axis with respect to handpiece 42. Rotation dial 60 is preferably connected to an outer cannula connector portion 88. In the embodiment of FIGS. 18-20, outer cannula connector portion 88 is a sleeve that is integrally formed with rotation dial 60 and which is fixedly secured to outer cannula 44 such as by an adhesive or other known connection means. In the exemplary embodiment of FIG. 20 rotation dial 60 has an outer diameter that is greater than that of sleeve 88. For ease of viewing, fluid supply sleeve 302 is not shown in FIG. 20.

As mentioned previously, inner cannula 76 includes a hinge 80 to allow inner cannula cutting section 83 to pivot toward outer cannula opening 49 when device 40 is in operation. In order to ensure the correct operation of hinge 80, the circumferential alignment of hinge 80 and outer cannula opening 49 should be maintained. Thus, rotation dial 60 is preferably connected to inner cannula 76 such that when rotation dial 60 is rotated, both outer cannula 44 and inner cannula 76 rotate in a fixed angular orientation with respect to one another by an amount that directly corresponds to the amount by which rotation dial 60 is rotated. Rotation dial 60 may be directly connected to inner cannula 76 or may use an intervening connecting device. However, rotation dial 60 should be configured to allow inner cannula 76 to reciprocate with respect to rotation dial 60. As best seen in FIG. 20, rotation dial inner cannula connector 86 may be provided to connect rotation dial 60 to inner cannula 76. Rotation dial inner cannula connector 86 comprises a proximal sleeve 87 disposed about inner cannula 76 and a distal, radially extending annular flange 90 with an outer diameter greater than that of the sleeve 87. Sleeve 87 and flange 90 may be in the shape of circular cylinders. Alternatively, and as shown in FIGS. 18-19, sleeve 87 and flange 90 may be in the shape of polygonal cylinders. Sleeve 87 is slidably received within the annular cavity 130 at the distal end 126 of the cannula transfer 74 and keyed to the inner surface of cannula transfer 74 at annular cavity 130 such that sleeve 87 can reciprocate with respect to cannula transfer 74 while causing cannula transfer 74 to rotate with sleeve 87 when rotation dial 60 is rotated. When inner cannula 76 is reciprocated, cannula transfer distal end 126 reciprocates with respect to sleeve 87, thereby variably adjusting gap "G" defined within annular cavity 130 (FIG. 20). Alternatively, cannula transfer distal end 126 may be slidably received in an annular cavity formed in sleeve 87 and may be keyed to the inner surface of the annular cavity so that cannula transfer may reciprocate with respect to sleeve 87 while still rotating with sleeve 87 when dial 60 is rotates.

As best seen in FIG. 20, rotation dial 60 includes a first annular cavity 61 that is sized to receive and engage flange 90 in a close fitting relationship. Rotation dial 60 may be press fit to flange 90. In addition, adhesive connections or mechanical connections may be used. Because rotation dial 60 is directly or indirectly connected to both outer cannula 44 and inner cannula 76, both cannulae rotate in direct correspondence to the rotation of rotation dial 60, thereby allowing the user to adjust the orientation of outer cannula opening 49 and inner cannula hinge 80 in a circumferential direction with respect to handpiece 42. As a result, surgeons need not rotate the entire tissue cutting device 40 to obtain the desired angular orientation.

Rotation dial 60, outer cannula 44, and inner cannula 76 are preferably configured for 360° rotation. In addition, tactile indicators are preferably provided on rotation dial 60 to allow a user to reliably determine the extent to which dial 60 has been rotated from a given starting point. The tactile indication may comprise surface features defined on or in the exterior surface of rotation dial 60. In one exemplary embodiment, depicted in FIGS. 18-20, a plurality of ridges 122 is provided around the circumference of rotation dial 60 to provide tactile indication. The ridges also act as grips and facilitate the surgeon's ability to rotate the dial 60 without transferring unwanted motion to the surgical site.

As mentioned previously, vacuum (sub-atmospheric pressure) is applied to tissue collector 58 to aspirate severed tissue samples through inner cannula 76 in the proximal direction. The application of vacuum to inner cannula 76 via tissue collector vacuum hose fitting 59 will have a propensity to produce a vacuum at proximal end 45 of outer cannula 44 if leakage occurs between inner cannula 76 and the components of upper housing 52. The generation of a vacuum at outer cannula proximal end 45 will in turn cause fluids and/or tissue samples at the distal end of outer cannula 44 to flow into the annular clearance between inner cannula 76 and outer cannula 44 that extends from its proximal end at outer cannula proximal end 45 to its distal end at inner cannula distal end 79. This fluid and/or tissue can result in blockage of the annular clearance and increased friction between the inner cannula 76 and outer cannula 44, resulting in degraded performance. Accordingly, a seal 129 is preferably provided to prevent air artifacts, fluid (water, saline, blood, etc.) flow, and tissue sample flow in the annular clearance between inner cannula 76 and outer cannula 44.

The seal 129 is preferably disposed adjacent the proximal end of the annular clearance between inner cannula 76 and outer cannula 44, i.e., proximally adjacent to outer cannula proximal end 45. As shown in FIG. 20, seal 129 is preferably annular and circumscribes inner cannula 76, extending from the outer surface of inner cannula 76 in a radially outward direction as well as longitudinally along a portion of the length of inner cannula 76.

In the embodiment of FIG. 20, rotation dial 60 and sleeve 87 act as a seal housing and include a seal cavity 131 which is an annular cavity disposed immediately adjacent to and distal of first annular cavity 61. Seal cavity 131 is sized to accept seal 129 therein. The seal 129 may be a conventional seal such as a solid, flexible and/or elastomeric o-ring. However, seal 129 is preferably amorphous and comprises a thixotropic material that is a semi-solid. It is further preferred that seal 129 fill the entirety of seal cavity 131 to ensure that cavity 131 is substantially leak free. In the exemplary embodiment of FIG. 20, seal cavity 131 has an outer diameter that is greater than the outer diameter of outer cannula 44. Moreover, the annular thickness of seal cavity 131 is preferably greater than the annular clearance between outer cannula 44 and inner cannula 76 to better ensure complete sealing of the annular clearance.

In one exemplary embodiment, seal 129 is a grease—such as the so-called "high vacuum greases"—that is formulated to withstand vacuum conditions. Suitable high vacuum greases include halogenated polymers. The halogenated polymers are preferably based on cyclic ether or unsaturated hydrocarbon polymeric precursors. In one exemplary embodiment, a perfluoropolyether (PFPE) grease is used. Examples of such greases include the FOMBLIN® family of greases supplied by Solvay Solexis, Inc. Other examples of such greases include polytetrafluroroethylene greases ("PTFE") such as TEFLON® greases supplied by DuPont. One suitable high vacuum grease is FOMBLIN® Y VAC3 grease, which is a PFPE grease with a PTFE thickener. The semi-solid seal 129 preferably has a kinematic viscosity at 20° C. of at least about 500 cSt, more preferably at least about 800 cSt, and even more preferably at least about 1200 cSt. Semi-solid seal 129 preferably has a kinematic viscosity at 20° C. of no greater than about 2500 cSt, more preferably no greater than about 2000 cSt, and even more preferably no greater than about 1700 cSt.

The use of a semi-solid seal 129 has several advantages. Because the seal is semi-solid, it will tend to absorb and dampen vibrations transmitted from the reciprocation of the inner cannula, thereby reducing overall vibration of device 40, and in particular, the vibration transmitted to outer cannula 44. The dampening of such vibrations is particularly beneficial because it reduces the transmission of unwanted vibrations to outer cannula 44 which can disturb delicate neurosurgical procedures. Moreover, because it is not a solid seal, seal 129 will experience less heating and wear as it is frictionally engaged by the reciprocating inner cannula 76. In certain embodiments, a portion of seal 129 will adhere to the outer surface of inner cannula 76 as it reciprocates producing a zero slip velocity condition at the inner cannula 76 outer surface which may further reduce frictional heating and degradation of seal 129. Because semi-solid seal 129 produces less frictional resistance to the reciprocation of inner cannula 76 as compared to conventional solid seals such as o-rings, it also decreases the required motor power consumption and can facilitate the use of lower torque and lower cost motors, which in turn facilitates making device 40 disposable.

In one configuration, device 40 is connected to a vacuum source and configured for variable aspiration, i.e., configured to supply variable levels of vacuum to inner cannula lumen 78. As depicted in FIG. 21A, in one exemplary implementation, a tissue cutting system is provided which comprises tissue cutting device 40, a tissue collector 58, a controller 132, a vacuum generator 153, a vacuum actuator 144, a controllable valve 146, a vacuum line 151, and a fluid collection canister 192. As mentioned previously, in FIG. 21A tissue collector 58 is located remotely from handpiece 42 and may be placed far enough from the handpiece 42 to remain outside of the sterile field during a tissue cutting operation. As best seen in FIG. 21B, tissue collector 58 is generally the same as the tissue collector 58 depicted in FIGS. 4-5. Vacuum line 151a connects the distal end of tissue collector 58 to proximally projecting portion 95 of seal holder 94 on the proximal end of tissue cutting device upper housing 52. In one arrangement, the proximal end of vacuum line 151a includes a hose fitting 59b that is integrally formed with a tissue collector coupler 296. Coupler 296 is similar in structure to tissue collector connector 96 (FIGS. 4-5) and is a cylindrical structure with a hollow interior for receiving a portion of tissue collector 58. As best seen in FIG. 21B, tissue collector 58 includes projections 202 and 204 which engage complementary slots 298 and 200 in coupler 296 in the same manner that projections 102 and 104 engage slots 98 and 100 in FIGS. 4-5. At the proximal end of tissue collector 58, hose fitting 59a engages vacuum line 151b which in turn is connected to fluid collection canister 192. Fluid collection canister 192 is connected to vacuum generator 153 via vacuum line 151c. Vacuum generator 153 is connected to controllable valve 146 by way of pressure line 147.

In yet another alternative arrangement, to provide nutrients for a biologically friendly, tissue efficacy prolonging environment to the resected tissue, referring to FIG. 21C, a preservation and tissue maintaining adapter system 500 may be positioned between tissue collector 58 and device 40. In one exemplary arrangement, preservation adapter system 500 is configured with a Y-shaped connector containing a valve element.

Figures 21D, 21E:
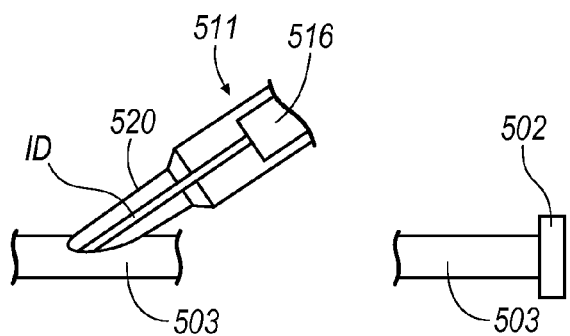
FIG. 21D is a partial cross-sectional view of the preservation adapter system of FIG. 21C.
FIG. 21E is a partial close-up view of a first connector of the preservation adapter system of FIG. 21C.

More specifically, preservation adapter system 500 includes a first connector element 502 (best seen in FIG. 21E) connected to a first end of a body portion 503 and a second connector element 504 connected to an opposite end of body portion 503. In one exemplary configuration, first connector element 502 may be configured to be received directly within an open proximal end of a fitting 505 connected to vacuum line 151a. In the exemplary configuration shown in FIG. 21C, an adapter element 506 connects first connector element 502 to fitting 505. In the exemplary configuration shown in FIG. 21C, adapter element 506 includes a first end 507 that is sized to receive, or otherwise connect to, first connector element 502 in any suitable manner, including, but not limited to, a threaded engagement. Adapter element 506 may be configured with an elongated body 508 that terminates in a second end 509. Second end 509 is configured to be received within an open proximal end of fitting 505. In the exemplary configuration shown in FIG. 21C, body 508 tapers from first end 507 to second end 509.

Second connector element 504 is configured to secure preservation adapter system 500 to tissue collector 58 via coupler 296. In one exemplary configuration, second connector end 504 is configured to be received within, or otherwise connected to a fitting 510. More specifically, fitting 510 includes a first end 512 that receives second connector element 504, in any suitable manner, and a second end 514 that is configured to connect to hose fitting 59b.

A needleless syringe port 511 intersects body portion 503. Port 511 is may be configured with a valve element 516 (shown in phantom) in communication with an opening 518 to port 511. Port 511 (and valve element 516) allow for introduction of solution to the tissue samples, while the tissue samples being deposited into tissue collector 58.

More specifically, preservation adapter system 500 is configured to permit a controlled flow rate of a solution into the tissue collector 58, and hence to permit the tissue samples to be bathed in this solution. In one exemplary configuration, regulation of the quantity of fluid flow that is delivered to the tissue within tissue collector 58 may be defined by an internal diameter ID of a connector neck 520, that is smaller than the flow channel defined by body portion 503. The fluid flow may also be controlled and/or restricted by an internal orifice (not shown), positioned within neck 520, whereby the orifice has a diameter that is smaller than the internal diameter ID of neck 520. Additionally, valve element 516, which may be provided as either fixed or adjustable valve, can be provided in-line with the internal diameter ID of neck 520. Alternatively, a flow control valve (adjustable or fixed) may be provided in a supply line that serves as a connection between port 518 and a source of preservation solution.

In operation, to assist in preservation of tissue samples, preservation adapter system 500 may be used to introduce a nutrient rich or preservative solution into the artificial environment of tissue collector 58 to keep the tissue samples properly hydrated and nourished. A source of suitable solution may be fluidly connected to port 518 via suitable fitting and fluid supply such that vacuum may draw the solution through valve 516 and internal diameter ID and into body 503, via vacuum line 151B. In another exemplary configuration, the solution introduced by preservation adapter system 500 may be chilled to further assist in preserving tissue for future oncological use, but may be metered (by valve 516 and/or internal diameter ID/orifice) to provide a specific flow rate for the solution being introduced.

Suitable fluids designed to maintain and/or preserve tissue samples for further use may be introduced via syringe. Alternatively, as suggested above, a solution may be automatically drawn into port 518 via the vacuum pressure supplied to tissue collector 58 via vacuum line 151B, thereby providing a consistent solution to the tissue samples.

As shown in FIG. 21C, vacuum line 151b is attached to tissue collector 58. In one exemplary arrangement, a connector element 522 having an open proximal end 524 is attached to vacuum line 151b. Connector element 522 may be fluidly connected to an inlet 523 (best seen in FIG. 21A) to deposit bodily fluids and excess solution within canister 192. However, to allow transport of excised tissue samples, while maintaining the aseptic environment in which the excised tissue samples are stored, connector element 522 is configured to be selectively released from inlet 523 and looped around and re-attached to hose fitting 59b. More specifically, hose fitting 59b is received within open proximal end 524, thereby creating a closed environment system that may be easily transported, without contacting the tissue samples. More specifically, this configuration provides an internally sterile/aseptic environment that is ingress proof from atmosphere conditions, while also being compliant with OSHA biohazard requirements such that tissue collector 58 provides a fluid/leak proof chamber that is safe for the staff handling tissue collector 58, as well as being compliant for easy transportation.

Returning to FIG. 21A, the outlet of tissue collection canister 192 is preferably substantially liquid free and is connected to vacuum generator 153 via vacuum line 151c. Thus, vacuum generator 153 is in fluid communication with tissue collector 58 and inner cannula lumen 78, thereby generating a vacuum at the proximal end 77 of inner cannula 76 to aspirate severed tissue samples from inner cannula distal end 79 to tissue collector 58. The level of vacuum generated by vacuum generator is preferably variable and selectively controllable by a user. Maximum vacuum levels of at least about 0 in Hg. are preferred, and maximum vacuum levels of at least about 1 in Hg. are more preferred. Maximum vacuum levels of at least about 5 in Hg. are even more preferred, and maximum vacuum levels of at least about 10 in Hg. are still more preferred. Maximum vacuum levels of at least about 20 in. Hg. are yet more preferred, and vacuum levels of at least about 29 in. Hg. are most preferred.

The controllable valve 146 and the vacuum generator 153 provide a means for continuously adjusting and controlling the level of vacuum applied to tissue collector 58 and the proximal end of inner cannula lumen 78. Controllable valve 146 is supplied with a pressurized gas, preferably air, or an inert gas such as nitrogen. In one exemplary embodiment, the pressure applied to controllable valve 146 is about 70 psi.

The system further includes an electrical controller 132 which receives and provides signals to the various components to control or monitor their operations. Controller 132 provides control signals to device 40 via motor drive control line 142 to activate or deactivate motor 62. An aspiration valve control line 150 extends from the controller 132 to the controllable valve 146 which provides pressure to the vacuum generator 153. Signals to the controllable valve 146 through line 150 are used to control the amount of vacuum applied to tissue collector 58.

Controller 132 also receives electrical signals from the various components of the system. For instance, a pressure transducer 148 associated with the aspiration controllable valve 146, sends a signal along line 152 to the controller 132. The signal is representative of the pressure supplied through controllable valve 146 to vacuum generator 153. Thus, the transducer 148 provides immediate feedback to the controller which can in turn provide signals to aspiration controllable valve 146.

The user can adjust the system operating parameters by using panel controls such as a console knob 138 and/or one or more depressible controllers, such as a foot pedal 144. In one embodiment, foot pedal 144 can be used to activate the motor 62 in device 40, causing the inner cannula 76 to reciprocate within the outer cannula 44. In another embodiment, foot pedal 144 can be used to control the vacuum level supplied from vacuum generator 153 to tissue collector 58 and inner cannula lumen 78. In yet another embodiment, foot pedal 144 can be used both to activate motor 62 and to control the vacuum level supplied from vacuum generator 153 to tissue collector 58. In one arrangement, foot pedal 144 is configured to variably increase the level of vacuum applied to tissue collector 58 from a minimum level to a maximum level as foot pedal 144 is depressed from a first position to a second position. In such an arrangement, the first position is one in which foot pedal 144 is not depressed all or is only slightly depressed, and the second position is one in which foot pedal 144 is fully depressed. In another embodiment, knob 138 is used to set a preselected maximum vacuum level applied by vacuum generator 153. Thus, by depressing foot pedal 144 from a first fully open position to a second fully closed position, a plurality (preferably a continuum) of vacuum levels can be supplied to tissue collector 58 with the maximum vacuum level being user adjustable via knob 138.

In one exemplary embodiment, foot pedal 144 includes two switches (not shown) for providing variable vacuum and activating motor 62. In another exemplary embodiment, once foot pedal 144 is partially depressed from an open or undepressed position, motor 62 is activated. In accordance with the embodiment, continued depression of foot pedal 144 activates vacuum generator 153. Foot pedal 144 preferably provides continuous movement between a fully open and a fully depressed position which in turn corresponds to a plurality, and preferably a continuum, of vacuum levels that are supplied to inner cannula lumen 78. Once foot pedal 144 is fully depressed, the vacuum level supplied to inner cannula lumen 78 corresponds to a previously selected maximum vacuum level.

In certain illustrative examples, the user will adjust the level of vacuum to achieve a desired level of "traction" in the tissue surrounding the tissue to be severed. As used herein, the term "traction" refers to the exertion of a pulling force on tissue surrounding the target tissue to be severed. In some instances, traction may be visualizable by the surgeon with the use of a magnification instrument, such as a microscope or an endoscope. The level of vacuum will also determine the amount of unsevered tissue that is drawn into outer cannula opening 49, and therefore, the size of the severed tissue snippets 112 (FIG. 14). Therefore, when fine shaving operations are desired, the vacuum level will be a relatively lower level than if debulking (large scale tissue removal) is performed. Of course, the pre-selected maximum vacuum level will also affect the maximum size of tissue that is drawn into outer cannula opening 49, and therefore, will affect the maximum size of severed tissue samples during any one operation. Also, the vacuum level may be adjusted based on the elasticity, fibrotic content, and hardness/softness of the tissue.

Console 134 may also include indicator lights 136, one of which indicates the activation of cutting and one of which indicates the activation of aspiration. Console 134 may further include an analog display 140 with readouts for "aspiration" and "cutter." The "aspiration" read out indicates the vacuum level supplied to tissue collector 58 from vacuum generator 153. The "cutter" read out indicates the speed of reciprocation of inner cannula 76. In one embodiment, a speed sensor is mounted in device 40 to determine the speed of reciprocation of inner cannula 76 and the sensor is input to controller 132.

As mentioned previously, when device 40 is used to perform a cutting operation, inner cannula 76 reciprocates within outer cannula opening 49 to sever tissue received within outer cannula opening 49. When a cutting operation is complete, it may be preferred to have inner cannula 76 come to rest at a position that is proximal of the proximal edge 53 of outer cannula opening 49 to ensure that tissue is not trapped between inner cannula distal end 79 and outer cannula cutting edge 51. However, in certain methods of use, tissue cutting device 40 may be used as an aspiration wand without cutting any tissue. In these embodiments, the stop position of the inner cannula distal end 79 within outer cannula opening 49 determines the open area of the outer cannula 44, and therefore, the aspiration levels that can be applied immediately adjacent outer cannula opening 49. Thus, in some preferred embodiments, the inner cannula stop position is user adjustable. Tissue cutting device 40 may be used to aspirate a variety of fluids associated with a neurosurgical procedure, including without limitation blood, saline, cerebrospinal fluid, and lactated ringer's solution. In certain examples, the inner cannula stop position is adjusted to provide a desired degree of aspiration, outer cannula 44 is positioned proximate a target tissue, and vacuum is applied to manipulate the target tissue and draw it into outer cannula opening 49. Outer cannula 44 is then moved to a desired location or orientation, thereby moving the target tissue to the desired location or orientation. Once the target tissue has been satisfactorily manipulated, a cutting operation is initiated. By using device 40 in this manner, target tissues can be drawn away from areas where tissue cutting operations are undesirable, and the cutting can be performed remotely from those areas.

Figure 24:
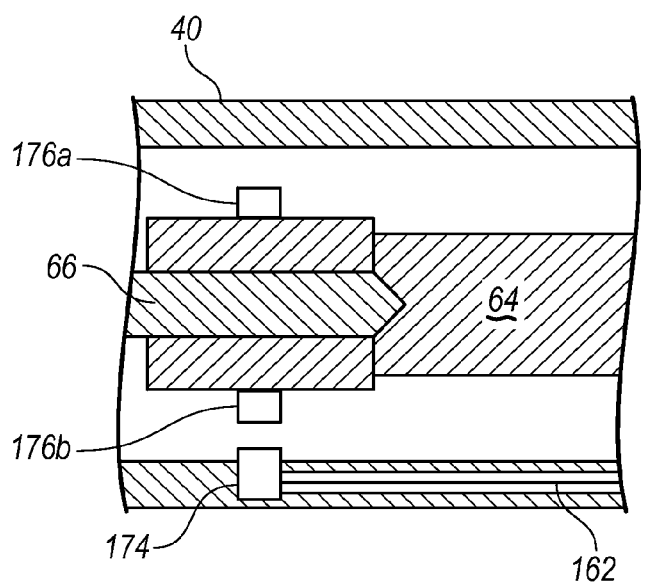
FIG. 24 is a partial cross-sectional view of the tissue cutting device of FIG. 1 depicting motor shaft position sensors for controlling a stop position of an inner cannula.

In one exemplary system, an inner cannula position control is provided which controls the rest position of inner cannula 76 when motor 62 is deactivated. Referring to FIG. 24, cam rotational position indicators 176a and 176b are mounted on the proximal end of cam 64. In an exemplary embodiment, cam rotational position indicators 176a and 176b are magnets having opposite poles. A position sensor 174 is mounted on the inner surface of cam housing 69 and generates a signal indicative of the rotational position of indicators 176a and 176b relative to position sensor 174. As mentioned previously, the rotation of cam 64 correlates directly to the position of inner cannula 76 within outer cannula 44. Thus, the rotation of cam 64 can be sensed to indirectly determine the position of inner cannula 76. Accordingly, indicators 176a/176b and sensor 174 can be used to determine the position of inner cannula 76 with respect to proximal edge 53 of outer cannula opening 49 (FIGS. 10-12).

Figure 22:
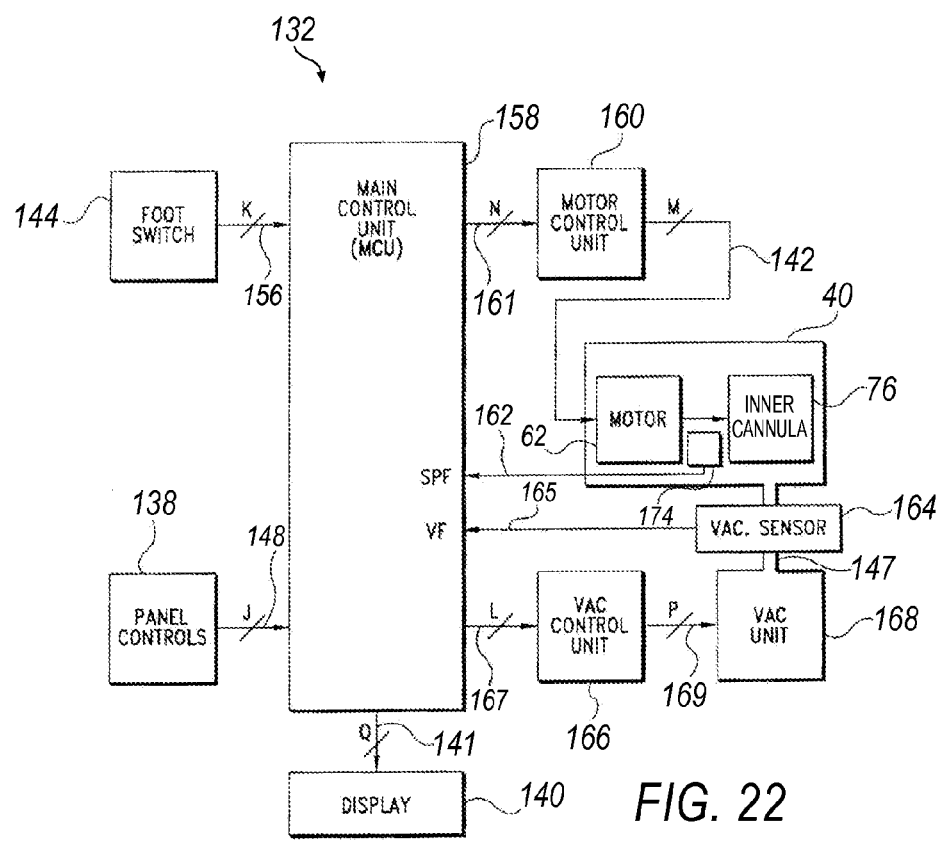
FIG. 22 is a block diagram of a control scheme for the tissue cutting system of FIG. 22.

Referring to FIG. 22, an embodiment of a system for controlling the operation of tissue cutting device 40 is provided. The system includes a main control unit 158 ("MCU"), which (in the embodiment shown) is configured as a microprocessor-based system. In one implementation, MCU 158 is incorporated in controller 132 (FIG. 21A) and is operable to control the various operations of the tissue cutting device 40. Foot switch 144 is electrically connected to a number of inputs of MCU 158 via an equal number, K, of signal paths 156, wherein K may be any integer. Panel controls, such as knob 138, are electrically connected to a number of inputs of MCU 158 via an equal number, J, of signal paths 145, wherein J may be any integer.

Display unit 140 is electrically connected to a number of outputs of MCU 158 via an equal number, Q, of signal paths 141, wherein Q may be any integer. In one exemplary implementation, depicted in FIG. 21A, display unit 140 is provided on console 134.

As mentioned previously, tissue cutting device 40 includes motor 62 coupled to the inner cannula 76 by an inner cannula drive assembly 63. The motor 62 is electrically connected to motor control unit 160 via a number, M, of signal paths 161 wherein M may be any integer. The motor control unit 160 is, in turn, connected to a number of outputs of MCU 158 via an equal number, N, of signal paths 161. Cam rotational position sensor 174 is electrically connected to a motor shaft position feedback input (SPF) of MCU 158 via signal path 162, and provides a motor stop identification signal thereon as will be more fully described hereinafter. The motor shaft stop identification signal provided by sensor 174 on signal path 162 preferably provides MCU 158 with a motor stop identification signal and may optionally provide a cutter speed signal that is proportional to the motor speed for a geared system or identical to the motor speed for a direct drive system.

Tissue cutting device 40 is further mechanically connected to a vacuum unit 168 (e.g., a combination of controllable valve 146 and vacuum generator 153 in FIG. 21A) via conduit 163 (not shown in FIG. 22), whereby the vacuum unit 168 provides a controllable vacuum level to device 40 for aspirating tissue received in inner cannula lumen 78. Vacuum unit 168 is electrically connected to a vacuum control unit 166 via a number, P, of signal paths 169 wherein P may be any integer. The vacuum control unit 166 is, in turn, connected to a number of outputs of MCU 158 via an equal number, L, of signal paths 167, wherein L may be any integer. A vacuum sensor 164, which may be a temperature compensated solid-state pressure sensor, may be positioned within the conduit 151 and electrically connected to a vacuum feedback (VF) input of MCU 158 via signal path 165. Alternatively, the vacuum sensor 164 may be disposed within hand piece 42 or within the vacuum unit 168 itself.

In operation, the MCU 158 is responsive to a vacuum command signal, preferably provided by a corresponding control mechanism associated with control panel 138, foot pedal 144, or an equivalent control mechanism, to provide one or more corresponding vacuum control signals to vacuum control unit 166 along signal paths 167. The vacuum control unit 166, in turn, is responsive to the one or more vacuum control signals to activate the vacuum unit 168 to thereby provide tissue cutting device 40 with a desired level of vacuum. The actual vacuum level provided to tissue cutting device 40 is sensed by vacuum sensor 164, which provides a corresponding vacuum feedback signal to the vacuum feedback input VF of MCU 158. The MCU 158 is then operable to compare the vacuum feedback signal with the vacuum command signal and correspondingly adjust the one or more vacuum control signals to achieve the desired vacuum level within tissue cutting device 40. Such closed-loop feedback techniques are well known in the control systems art.

In one alternative embodiment, the MCU 158 can be replaced by individual microprocessors controlling the input and output for controlling the operation of the motor 62 and the vacuum unit 168. In this alternative embodiment, the motor control and vacuum control microprocessors can be PIC16CXX Series microcontrollers provided by Microchip, Inc. of Chandler Ariz. The motor control microcontrollers can receive input signals from the motor driver 172 (FIG. 23) and position sensor 174, as well as the foot switch 144 and panel controls 138. Likewise, the vacuum microcontroller can receive input signals from the vacuum sensor 164, the foot switch 144 and panel controls 138. Each microcontroller can provide its own output to its driven component and have its own display, such as an LED display, indicative of its operational status. Moreover, the two units can communicate with each other to ensure clean cutting by proper timing of the cutting and aspiration functions.

Figure 23:
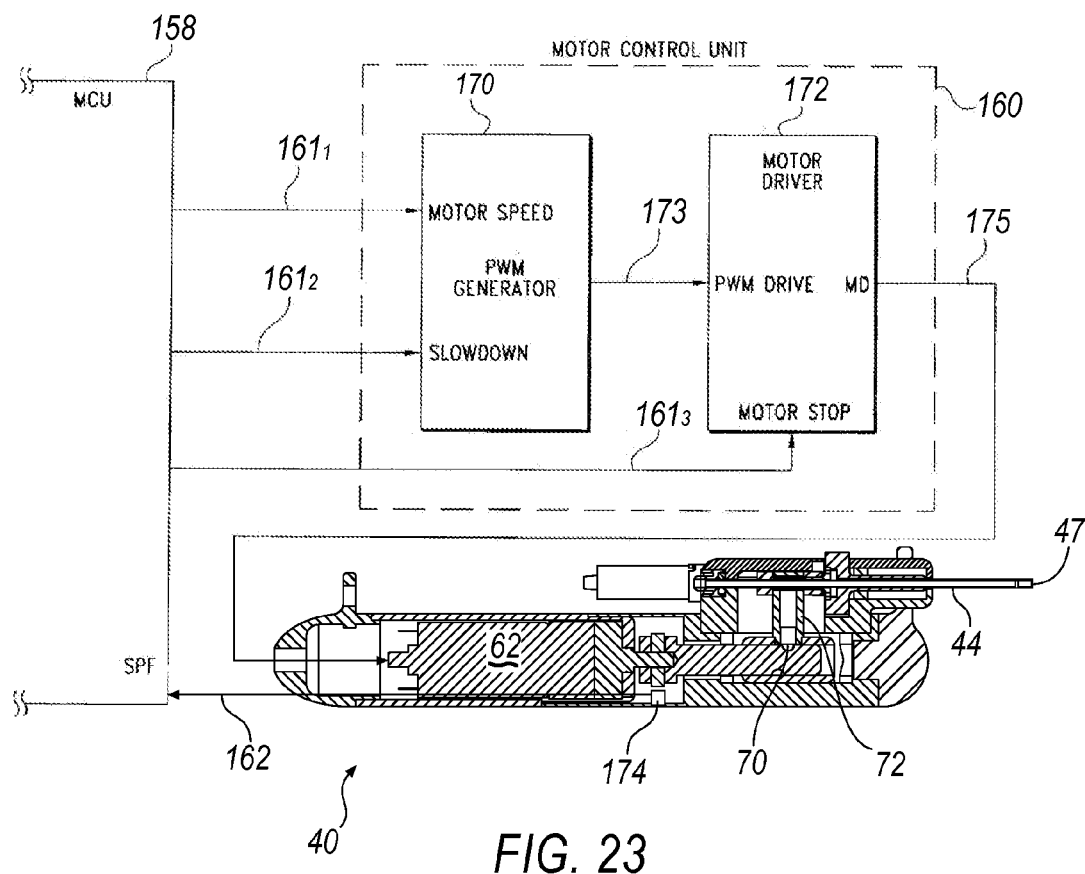
FIG. 23 is diagram of the tissue cutting device of FIG. 1 and the motor control unit of FIG. 22.

Referring now to FIG. 23, one exemplary embodiment of the motor control unit 160 is shown in greater detail. The motor control unit 160 in one embodiment includes a pulse width modulation (PWM) generator circuit 170 having a motor speed input connected to one of the MCU outputs $161_1$. If motor speed control is provided, the output $161_1$ can provide a variable voltage signal indicative of a desired motor speed and based upon the position of a throttle, foot pedal, or other actuator. In certain embodiments, an additional input is connected to another one of the MCU outputs $161_2$. The signal at this output $161_2$ can be a motor slowdown signal as described below. Alternatively, the output $161_2$ can constitute a braking signal used in connection with a current feedback motor controller. As a further alternative, the slowdown command may be communicated via the motor speed command itself, rather than through a separate signal $161_2$. In this instance, the output $161_2$ may not be required.

In the illustrated embodiment, the PWM is disposed within the motor control unit 160. Alternatively, the PWM can be integrated into the MCU 158, or into the separate motor control microprocessor discussed above. In embodiments that include motor speed control, the motor speed input receives a motor speed signal from MCU 158 indicative of desired operational speed of the motor 62. The slowdown input can receive a speed adjustment signal from the MCU 158 based on an actual motor speed signal provided by a motor sensor associated with the motor 62.

A motor driver circuit 172 is electrically connected to PWM generator circuit 170 via signal path 173 and receives a PWM drive signal therefrom, which is a pulse width modulated signal indicative of desired motor speed. The motor driver circuit 172 provides a motor drive signal (MD) to motor 62 via signal path 175. While the disclosed embodiment contemplates digital control of the motor using the PWM generator circuit 170, alternative embodiments can utilize closed loop feedback analog circuits, particularly where slower cutting speeds are contemplated.

The motor drive signal includes a motor stop input that is connected to another one of the MCU outputs $161_1$. In accordance with an aspect of the present disclosure, MCU 158 provides a motor stop signal on signal path $161_3$, based on a motor deactivation command provided by foot switch 144 or panel control 138 and also based on a motor stop identification signal provided by sensor 174, to stop the inner cannula 76 in a desired position, as will be more fully described hereinafter. In certain embodiments, only the motor stop signal is utilized to command the motor to stop at the predetermined position. In these certain embodiments, the motor slowdown signal on path $161_2$ can be eliminated, or the input on path $161_2$ can be used for other control signals to the motor control circuit.

Figure 25:
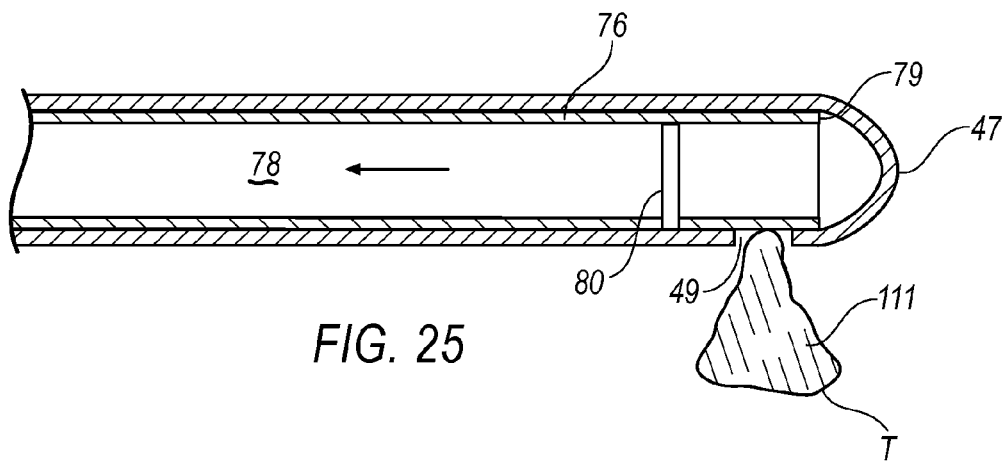
FIG. 25 is a partial cross-sectional view of the outer cannula and inner cannula of the tissue cutting device of FIG. 1 with the inner cannula in a first position relative to the outer cannula.
Figure 26:
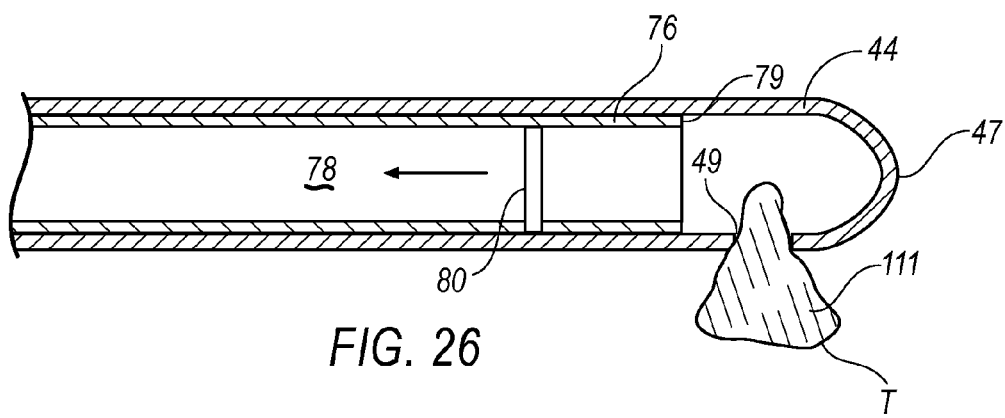
FIG. 26 is a partial cross-sectional view of the outer cannula and inner cannula of the tissue cutting device of FIG. 1 with the inner cannula in a second position relative to the outer cannula.
Figure 27:
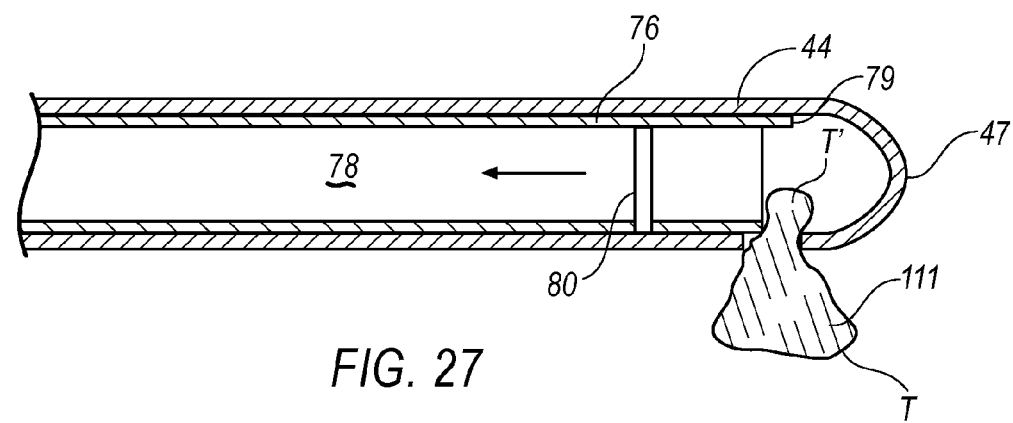
FIG. 27 is a partial cross-sectional view of the outer cannula and the inner cannula of the tissue cutting device of FIG. 1 with the inner cannula in a third position relative to the outer cannula.
Figure 34:
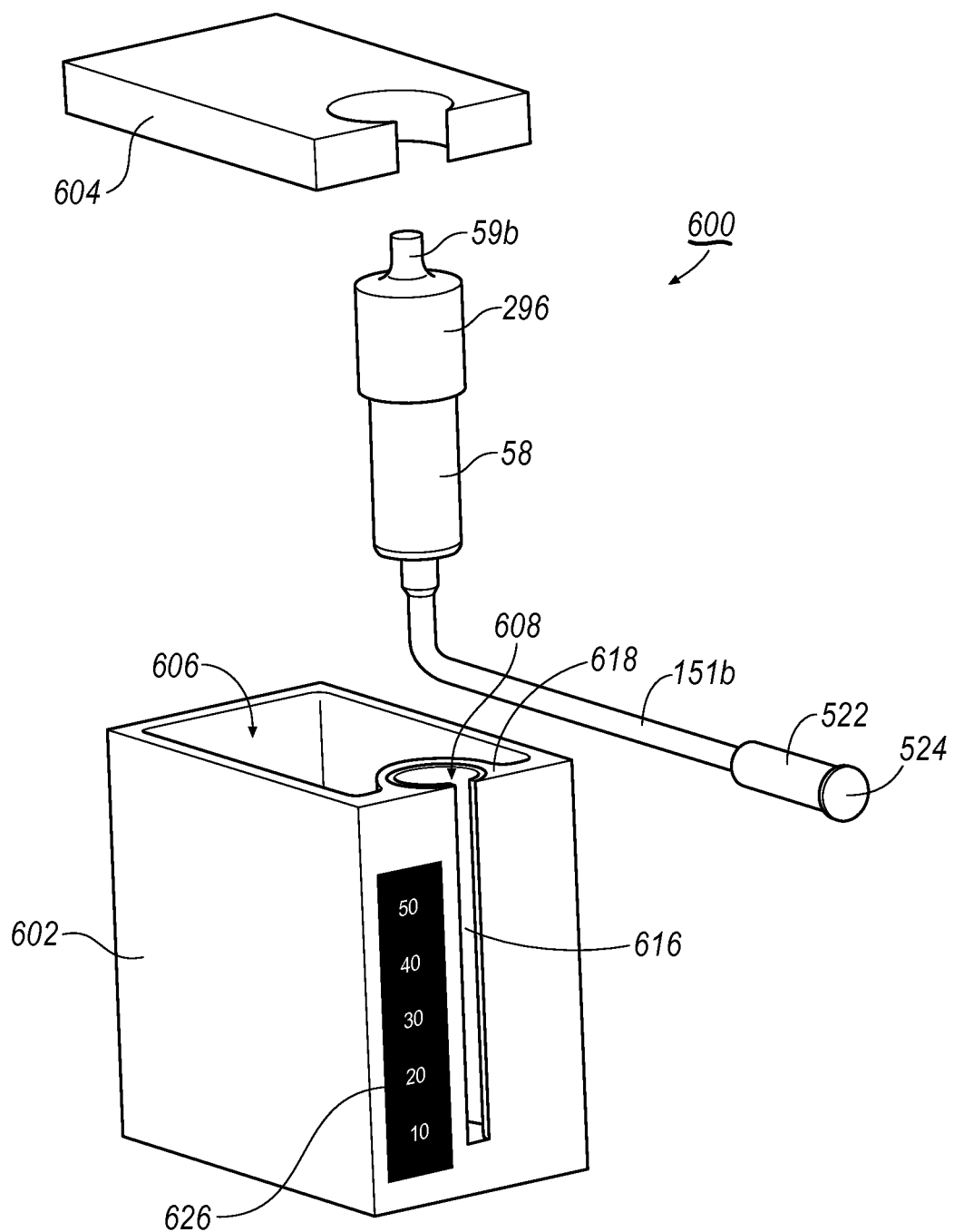
FIG. 34 is an exploded view of a cooling system for use with a tissue collector.
Figure 35:
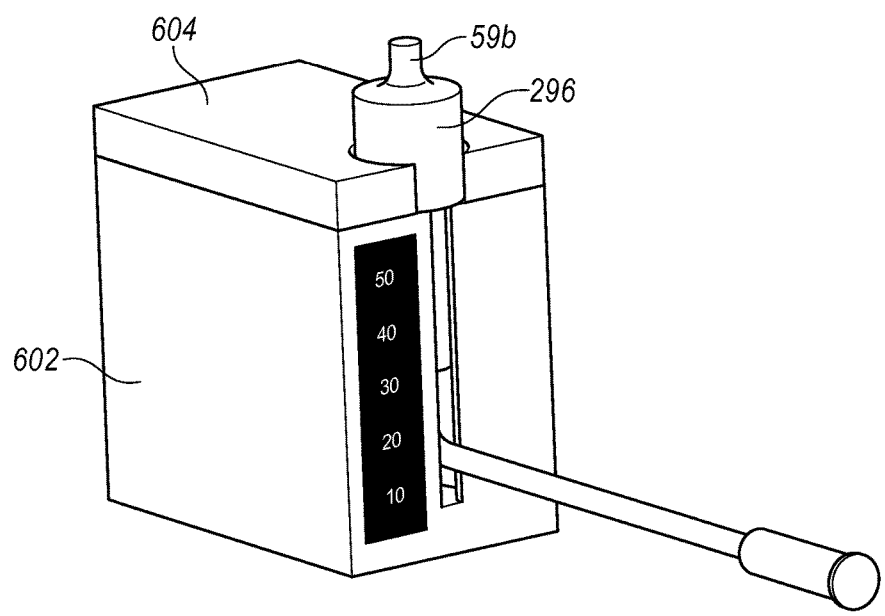
FIG. 35 is a perspective view of the cooling system of FIG. 34 with the tissue collector positioned therein.
Figure 36:
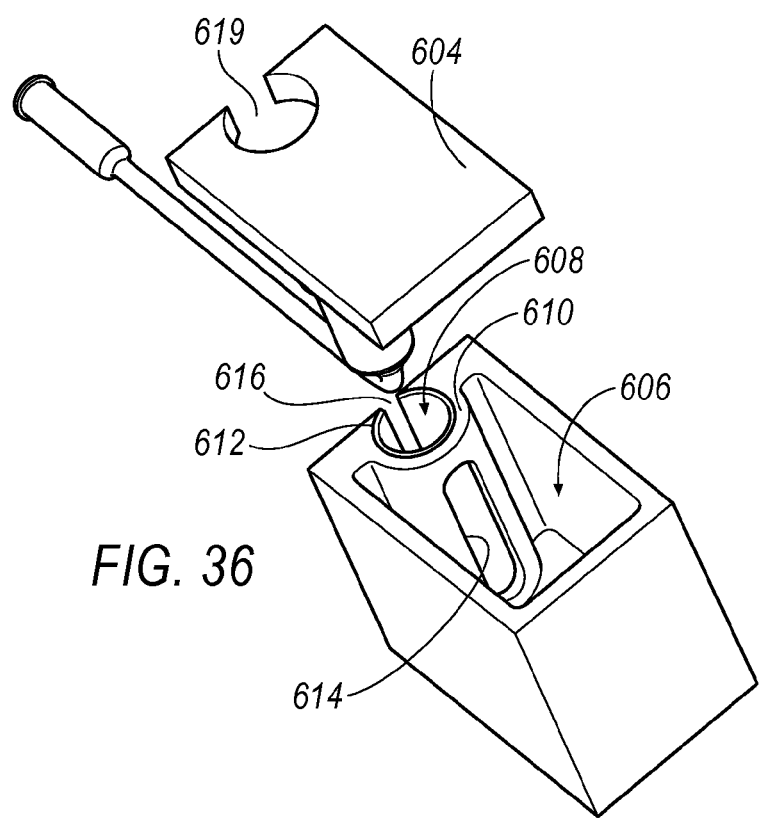
FIG. 36 is a partial exploded perspective view looking into the cooling system of FIG. 34.
Figure 37:
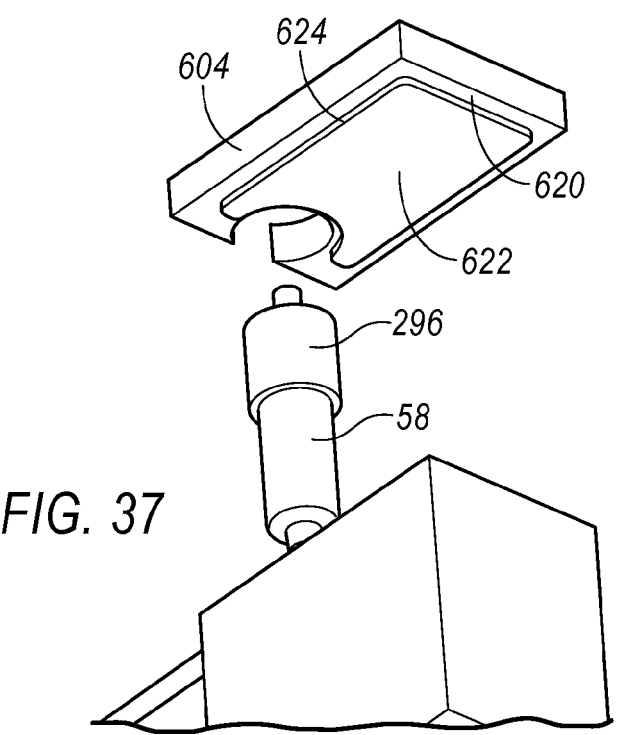
FIG. 37 is a partial exploded perspective view looking at the bottom surface of an exemplary lid that may be used with the cooling system of FIG. 34.

As mentioned previously, when tissue cutting device 40 is deactivated, inner cannula 76 may come to rest partially disposed within outer cannula opening 49. Referring to FIGS. 25-27, three different stop positions of inner cannula 76 are shown. For ease of viewing, fluid supply sleeve 302 is not shown. FIG. 27 shows that inner cannula 76 can be stopped in a position in which a portion of the tissue T is trapped between the outer cannula opening 49 and the inner cannula distal end 79. Efforts at withdrawing outer cannula 44 from the surgical site may accordingly result in tearing of the tissue portion T' away from the surrounding tissue base T. Surgeons encountering such trapping would typically be required to re-activate tissue cutting device 40 to release the tissue portion T' from the surrounding tissue base T. To prevent such tissue trapping from occurring, deactivation of the motor 62 is controlled in such a manner that the inner cannula distal end 79 is positioned remotely from the outer cannula opening 49 when inner cannula 76 stops reciprocating. However, in certain methods of use, device 40 is used as an aspiration wand. In those methods, the stop position of inner cannula distal end 79 may be adjusted to different locations within outer cannula opening 49 in order to adjust the level of aspiration supplied to a region of the anatomy proximate outer cannula opening 49. For example, stop positions may be selected that limit the percent open area of outer cannula opening 49 to 25%, 50%, or 75% of the total area of opening 49.

Referring again to FIGS. 23 and 24, controlled deactivation of the motor 62 will now be described in detail. When it is desired to deactivate tissue cutting device 40, a motor stop command is provided such as via foot switch 144 or a panel control 138. In one embodiment, MCU 158 is responsive to the motor stop command to provide a slowdown signal to the PWM generator via signal path 161$_2$ which slows the action of motor 62. Preferably, the slowdown signal corresponds to a predefined signal level operable to drive the motor 62 at a motor speed below a motor speed threshold level. Since motor 62 is a brushed DC motor, it has a rotational resistance or resistive torque associated therewith as described above. In addition, in some cases friction between the inner cannula 76 and outer cannula 44 will increase the rotational resistance. Due to this combined rotational resistance, operation of the motor 62 will cease very rapidly or nearly instantly if the motor drive signal on signal path 142 is disabled while driving motor 62 below the motor speed threshold. Accordingly, when device 40 is used to cut tissue, alignment of position indicators 176a or 176b with sensor 174 preferably corresponds to a position of the tissue cutting device 40 at which there is no danger of trapping tissue between inner cannula distal end 79 and the outer cannula opening 49, and sensor 174 is operable to produce the motor stop identification signal when so aligned with indicator 176a or 176b.

In one embodiment, MCU 158 is operable to produce a motor stop signal on signal path 161$_3$ when sensor 174 detects alignment of position indicators 176a or 176b therewith after one passage thereby of indicator 176a or 176b since producing the slowdown signal on signal path 161$_2$. Allowing one passage of indicator 176a or 176b by sensor 174 after issuing the slowdown signal ensures that the rotational speed of motor 62 is at or below the motor speed threshold when subsequently issuing the motor stop command, regardless of the position of indicator 176a or 176b relative to sensor 174 when the slowdown command was issued. After one passage of indicator 176a or 176b by sensor 174 since issuing the slowdown signal, MCU 158 is responsive to the signal provided by sensor 174 indicative of alignment of indicator 176a or 176b therewith, to produce the motor stop signal on signal path 161$_3$. The motor driver 172 is responsive to the motor stop signal to produce a motor disable signal on signal path 175. Due to the inherent rotational resistance, motor 62 is responsive to the motor disable signal to immediately cease operation thereof with indicator 176a or 176b substantially aligned with sensor 174, and with the inner cannula 76 accordingly positioned so as not to trap tissue between inner cannula distal end 79 and the outer cannula opening 44.

As mentioned above, in one exemplary embodiment, the inner cannula stop position is user adjustable, such as by adjusting a panel control 138 on console 134. In accordance with the embodiment, it is contemplated that the stopped rotational position of cam 64, and therefore the inner cannula distal end 79, may be instead aligned with a predetermined differential distance between the indicator 176a/176b and the sensor 174. The braking characteristics of the inner cannula 76 and motor 62 can be ascertained and the stopping distance determined so that this predetermined differential distance can be calibrated accordingly. However, in a preferred embodiment, when inner cannula 76 comes to rest, the distal end 79 is located proximally of the outer cannula opening 44 by a predetermined distance, as shown in FIG. 26.

A method of using device 40 to perform a tissue cutting procedure will now be described in the context of a neurosurgical procedure involving the cutting of a neurological target tissue. In one example, the target tissue is brain tissue, and in another example the target tissue is spinal tissue, for example, the tissue of an intervertebral disk. In certain exemplary methods, the tissue specimen being cut is a tumor or a lesion.

In accordance with the method, it is first determined whether the cutting operation will be a debulking operation, a fine shaving operation, or a cutting operation that is somewhere in between a debulking and fine shaving operation. A surgical access path is then created to the tissue sample of interest. In one embodiment, the surgical path is created and/or the target tissue is accessed using an "open" procedure in which the target tissue is open to the atmosphere (e.g., a full open craniotomy). In another embodiment, the surgical path is created and/or the target tissue is accessed using a "closed" procedure in which the target tissue is sealed from the atmosphere.

At this point, the distal end 79 of inner cannula 76 is located proximally of outer cannula opening 49 due to the use of an inner cannula stop position control of the type described previously. The maximum vacuum level to be applied to device 40 is then set using panel controls 138. Generally, higher vacuum levels will be used for debulking procedures than for fine shaving procedures as higher vacuum levels will tend to draw relatively larger sections of tissue into outer cannula opening 49. In one embodiment, the panel control 138 is a knob on console 134 that is rotated to set the desired maximum vacuum level.

In one arrangement, device 40 is configured to be gripped with a single hand during a tissue cutting procedure. Thus, the surgeon will grasp handpiece 42 in the fingers of one hand and insert outer cannula 44 to a location proximate the target tissue. Depending on the hand and the surgeon's orientation with respect to the target tissue, the surgeon may then rotate dial 60 to rotate outer cannula 44 about its own longitudinal axis and orient outer cannula opening 49 immediately adjacent the target tissue. The rotation of outer cannula 44 with dial 60 causes inner cannula 76 to rotate such that a fixed rotational or angular relationship is maintained between inner cannula 76 and outer cannula 44. Once the opening is in the desired orientation, the motor 62 is activated, for example, by beginning to depress pedal 144 from its fully undepressed (open) position to a second partially depressed position which causes motor control unit 160 to send a signal to motor 62 on signal path 142. Motor 62 may also be activated by a panel control 138. The rotation of motor 62 causes cam 64 to rotate, resulting in the reciprocation of cam follower 68 and cam transfer 72. The reciprocation of cam transfer 72 causes cannula transfer 74 to reciprocate, thereby reciprocating inner cannula 76 within outer cannula lumen 110.

Once motor 62 is activated, vacuum is supplied to inner cannula lumen 78. In one embodiment, as the pedal 144 is further depressed (beyond the position at which motor 62 is activated), vacuum generator 153 is activated. The surgeon then adjusts the degree of depression of the foot pedal 144 to obtain the desired level of vacuum by visualizing the movement of the target tissue relative to the outer cannula opening 49. In certain embodiments, the surgeon controls the vacuum level to obtain a desired amount of traction in the tissue surrounding the target tissue. If the surgeon desires to apply the previously set maximum vacuum level, he or she depresses pedal 144 to its fully depressed position.

If desired, the surgeon may depress and partially release the pedal 144 a number of times to manipulate the target tissue in a satisfactory manner. Vacuum controller 166 is manipulable to adjust the setpoint of vacuum generator 153 which is manipulable to adjust the inner cannula vacuum level along a continuum of levels below the pre-selected maximum level. In one embodiment, the extent of depression of foot pedal 144 dictates the vacuum set point supplied to vacuum control unit 166 on signal path 167, and therefore, the amount of vacuum provided by vacuum unit 168. Vacuum sensor 164 measures the vacuum supplied to tissue collector 58 and feeds a signal back to main control unit 158 on signal path 165. The measured vacuum is then compared to the set point applied to vacuum control unit 166 via foot pedal 144, and the signal transmitted to vacuum generator 153 is then adjusted to move the measured vacuum value towards the set point. To obtain a vacuum level equal to the maximum pre-set level, pedal 144 is completely depressed. Maximum vacuum levels of at least about 0 in Hg. are preferred, and maximum vacuum levels of at least about 1 in Hg. are more preferred. Maximum vacuum levels of at least about 5 in Hg. are even more preferred, and maximum vacuum levels of at least about 10 in Hg. are still more preferred. Maximum vacuum levels of at least about 20 in. Hg. are yet more preferred, and vacuum levels of at least about 29 in. Hg. are most preferred.

Due to the resistance of the tissue drawn into outer cannula opening 49, cutting section 83 pivots about hinge 80 and toward outer cannula opening 49 as inner cannula 76 travels in the distal direction. The inner cannula cutting section 83 continues to pivot as it travels in the distal direction, eventually compressing tissue within outer cannula opening 49 and severing it. The severed tissue forms a continuum of tissue snippets 112 (FIG. 14) within inner cannula lumen 78. Due to the vacuum applied to tissue collector 58, snippets 112 are aspirated through inner cannula lumen 78 in the proximal direction. They eventually exit inner cannula lumen 78 at inner cannula proximal end 77 and enter tissue collector 58 (or fluid collection canister 192 if no collector 58 is provided). Any fluids that are aspirated exit tissue collector 58 and are trapped in fluid collection canister 192. The surgeon preferably severs tissue at a cutting rate of at least about 1,000 cuts/minute. Cutting rates of at least about 1,200 cuts/minute are more preferred, and cutting rates of at least about 1,500 cuts/minute are even more preferred. Cutting rates of less than about 2,500 cuts/minute are preferred. Cutting rates of less than about 2,000 are more preferred, and cutting rates of less than about 1,800 cuts/minute are even more preferred.

The surgeon may move device 40 around the target tissue until the desired degree of cutting has been completed. Motor 62 is then deactivated, for example, by completely releasing pedal 144 so it returns to its fully undepressed (open) position. If an inner cannula stop position control is provided, inner cannula 76 preferably comes to rest proximally of outer cannula opening 49, as shown in FIG. 26. Outer cannula 44 is then removed from the surgical site. Tissue collector 58 is then removed from upper housing 52 of handpiece 42, and the collected tissue samples are either discarded or saved for subsequent analysis. Fluids collected in canister 192 are preferably discarded. If the remote tissue collector of FIG. 21A is used, tissue samples may be removed from it without removing outer cannula 44 from the surgical site or otherwise disturbing the surrounding tissue.

As mentioned previously, tissue cutting device 40 includes a fluid supply sleeve 302 which is selectively disposable about outer cannula 44 (i.e., the user can install or remove fluid supply sleeve 302 from outer cannula 44) to provide fluid to a surgical site. As best seen in FIGS. 28-31, fluid supply sleeve 302 includes an elongated channel section 304 that comprises an outer cannula channel 314 and at least one fluid supply channel through which fluids may pass. In the depicted embodiment, the at least one fluid supply channel is fluid supply channel 312. When the fluid supply sleeve 302 is in an uninstalled condition (e.g., FIG. 28), the fluid supply channel 312 may be separated from the outer cannula channel 314 along all or a portion of the length of elongated channel section 304 by a barrier wall, membrane, etc. However, in the example of FIG. 30, the outer cannula channel 314 is in fluid communication with the fluid supply channel 312 along the entire length of elongated channel section 304 when the fluid supply sleeve 302 is in an uninstalled condition. As best seen in FIG. 30, when fluid supply sleeve 302 is in an installed condition, outer cannula 44 occupies outer cannula channel 314 and effectively separates outer cannula channel 314 from fluid supply channel 312.

Referring to FIG. 1, hub 306 is connected to a fluid supply line 308, which is preferably a length of flexible, plastic tubing. Fluid supply line 308 includes a fluid source connector 310 on its proximal end. Fluid source connector 310 may be any known type of connector suitable for providing fluid flow. In the embodiment of FIG. 1, fluid source connector 310 is a male luer fitting.

Hub 306 may be connected to elongated channel section 304 in a variety of ways. One example is depicted in FIG. 29. As shown in the figure, proximal end 317 of elongated channel section 304 is connected to and disposed in the interior of hub 306. Hub 306 preferably includes a complementary channel (not separately shown) in which proximal end 317 of elongated channel section 304 is interfitted. The connection between elongated channel section 304 and hub 306 may be made in a variety of ways, including with adhesives and mechanical fasteners. In addition, elongated channel section 304 may be integrally formed with hub 306 such as by integrally molding elongated channel section 304 and hub 306 as a single piece. In the embodiment of FIG. 29, elongated channel section 304 and hub 306 are separately formed and then connected with an adhesive.

Hub 306 is generally cylindrical in shape. Hub 306 also includes a proximal opening 322 and a distal opening 323. Outer cannula 344 slidably projects through proximal end opening 322 and distal end opening 323. However, at distal hub end opening 323, outer cannula 44 projects through elongated channel section 304 of fluid supply sleeve 302. As shown in FIG. 1, in one exemplary configuration, the distal end 47 of outer cannula 44 projects through and away from the distal end 320 of elongated channel section 340 when fluid supply sleeve 302 is in an installed condition on outer cannula 44. An interior channel (not separately shown) is formed in the interior of hub 306 to retain outer cannula 44. Hub 306 may also include exterior surface features which enhance the user's ability to grip the hub such as when fluid supply sleeve 302 is being slid along outer cannula 44 to reposition fluid supply sleeve 302 along the length of outer cannula 44. In one example, a plurality of longitudinally oriented grooves are spaced apart from one another around the circumference of hub 306 and are provided to facilitate gripping. In another example, a plurality of protruding axially oriented ridges are provided and are spaced apart around the circumference of hub 306.

Fluid supply port 316 is provided along the length of hub 306 and is connected to fluid supply line 308. Fluid supply port 316 may comprise an opening in hub 306 and may also include a projecting connector or flange for securing fluid supply line 308 therein. Interior fluid channel 318 is provided in hub 306 and is in fluid communication with fluid supply port 316 and with fluid supply channel 312 via open proximal end 319 in fluid supply channel 312. Elongated channel section 304 includes a distal end opening 313 in the fluid supply channel 312 through which fluid is discharged to the surgical site, typically at or proximate to a target tissue being resected.

Elongated channel section 304 is preferably rigid or semi-rigid and made of a material that is suitable for use with sterilization techniques, such as ethylene oxide sterilization, Sterrad, autoclaving and gamma radiation sterilization. These include resins and metals. One type of suitable polymer material is heat shrinkable tubing. Additional suitable classes of polymers for forming elongated channel section 304 include gamma-compatible polyimides and polyamides, such as Kapton® polyimides supplied by DuPont, and Nomex polyamides supplied by DuPont. Polyester and polyethylene heat shrink tubing are also suitable classes of polymer materials. One exemplary class of heat shrink tubing is polyethylene terephthalate (PET) heat shrink tubing supplied by Advanced Polymers, Inc. Suitable materials for forming hub 306 include stainless steel, aluminum, and polymeric materials such as silicone polymers, and natural or synthetic rubbers.

As shown in FIG. 30, outer cannula channel 314 is partially-cylindrical and defines a partially circular cross-section. Fluid supply channel 312 may also be partially-cylindrical. However, in the example of FIG. 30, fluid supply channel 312 is generally in the shape of a partial elliptic cylinder (i.e., a cylinder with a partial elliptical cross-section). Inwardly directed ridges 324 and 326 define a transition between outer cannula channel 314 and fluid supply channel 312 along the length of fluid supply sleeve 302.

As mentioned previously, in one example, elongated channel section 304 is formed from heat shrink tubing. In certain embodiments, the heat shrink tubing is provided as a cylindrical length of tubing and is then modified to provide a dual channel structure such as the one depicted in FIG. 30. The dual channel structure may be provided by disposing the cylindrical heat shrink tubing around a mandrel having the cross-section of elongated channel section 304 which is depicted in FIG. 30 and applying heat to shrink the cylindrical tubing and conform its cross-section to that of FIG. 30.

In one preferred example, when fluid supply sleeve 302 is in an installed condition on outer cannula 44, outer cannula 44 may be rotated with respect to fluid supply sleeve 302. In one illustrative example, the surgeon may grip hub 306 with the fingers of one hand to restrain its rotational movement and rotate outer cannula rotation dial 60 with the thumb and/or fingers of the other hand to adjust the circumferential position of outer cannula opening 49. While fluid supply sleeve 302 may be configured to rotate with outer cannula 44, in many instances it is preferable to maintain the circumferential orientation of fluid supply sleeve 302 in order to prevent fluid supply line 308 from twisting. As shown in FIG. 1, in one preferred orientation, fluid supply sleeve 302 is circumferentially oriented such that fluid supply channel 312 is disposed between the longitudinal axis $L_1$ of handpiece lower housing 50 and outer cannula channel 314 in a direction that is substantially perpendicular to handpiece lower housing longitudinal axis $L_1$. In one example, wherein fluid supply sleeve 302 is used to deliver a hemostatic agent, it is preferable to orient fluid supply channel 312 such that it is spaced apart from outer cannula opening 49 in a direction perpendicular to the lower housing longitudinal axis $L_1$ (see FIG. 31) to prevent the aspiration of the hemostatic agent through outer cannula opening 49. However, other fluid supply channel 312 orientations may be used depending on the procedure involved.

Fluid supply sleeve 302 may be connected to a fluid source via fluid supply connector 310. The fluid source may be pressurized or unpressurized. Unpressurized fluids may be elevated to provide the necessary hydrostatic head to deliver the fluids through fluid supply channel 312.

A variety of different fluids may be delivered to a target tissue or proximate to the target tissue. In one example, irrigants such as saline are used to hydrate tissue at the surgical site, as well as to provide hydration of the tissue while the excised tissue sample is being aspirated. Further, in other exemplary arrangements, the fluid supply operatively connected to the fluid supply sleeve may include a nutrient-rich solution configured to maintain the viability of the samples excised by device 40. In yet another example, chilled fluid may be provided through fluid supply sleeve 302 designed to preserve excised tissue being aspirated through device 40. Saline elevated in temperature may also function as a hemostatic agent to initiate a "clotting cascade" which ultimately leads to the clotting of ruptured blood vessels in tumors or other tissues at the surgical site. Other hemostatic agents, sealants, and/or tissue adhesives may also be delivered to a surgical site via fluid supply channel 312. Examples include liquid embolic systems such as Neucrylate, a cyanoacrylate monomer derivative supplied by Valor Medical. Neurcrylate is delivered as a liquid and forms a spongy, solid material upon contacting blood. Another example of a suitable hemostatic agent is supplied by Medafor, Inc. under the name Arista AH Absorbable Hemostat. Arista AH functions as a molecular filter by separating serum from cellular constituents. It absorbs water from the blood and forms a gel matrix that slows blood flow and serves to enhance clotting.

Fibrin sealants may also be delivered to a surgical site via fluid supply channel 312. One suitable hemostatic matrix sealant is FloSeal®, a fibrin sealant comprising human thrombin which is supplied by Baxter Hyland Immuno. Another suitable sealant is Tisseel, a VH Fibrin Sealant comprising human thrombin, human fibrinogen, and bovine aprotinin. Certain sealants may comprise two or more fluid components that are mixed at or near the site of delivery. In such cases, the at least one fluid supply channel 312 preferably comprises two or more fluid supply channels that contain the respective two or more fluid components which are mixed at open distal end 313 of fluid supply channel 312. For fluids that are viscous and/or or gel-like in nature, a source of pressure such as a pump is preferably provided to delivery them through fluid supply channel 312 to the tissue.

Synthetic sealing agents may also be delivered via fluid supply channel 312. One such example is CoSeal, a hydrogel comprising 2 polyethylene glycol polymers supplied by Baxter. The 2 polymers are preferably delivered via two separate fluid delivery channels and chemically bond to one another on mixing to form a mechanical barrier that slows bleeding. Another suitable synthetic seal is Duraseal, which is supplied by Confluent Surgical. Duraseal comprises a polyethylene glycol polymer ester solution that is mixed at the point of delivery with a trilysine amine solution. Thus, fluid supply sleeve 302 is preferably provided with two fluid delivery channels to facilitate mixing of the two solutions at the point of delivery.

As mentioned above, in certain examples, it may be desirable to include two or more fluid supply channels in fluid supply sleeve 302. However, the two or more fluid supply channels need not be entirely separate along the length of sleeve 302. Instead, they may combine to form a single channel mixing zone at a defined distance from distal end opening 313. The length of such a mixing zone is preferably selected to ensure thorough mixing without allowing the fluids to form a solidified mixture prior to discharge from fluid supply sleeve 302.

Tissue adhesive glues are another category of fluids that may be delivered via fluid supply sleeve 302. Suitable tissue adhesive glues include those formed from formaldehyde or glutaraldehyde-based tissue adhesive glues. One suitable type of glutaraldehye based tissue adhesive glue is Bio-Glue® a protein hydrogel comprising bovine serum albumin, glutaraldehyde, and water which is supplied by Cryolife, Inc. Depending on the viscosity of the tissue adhesive glue, pressurized delivery may be required.

In certain examples, elongated channel section 304 is formed with an imageable material to facilitate the identification of its position within the patient. In one example, elongated channel section 304 includes an MRI-imageable material. In another example, elongated channel section 304 includes a positron emission tomography (PET) imageable material such as a radioactive isotope. Suitable isotopes include halogenated sugars such as [$^{18}$F]fluorodeoxyglucose and isotopes of amino acids such as [$^{11}$C]methionine. In one example, PET imaging is performed while fluid supply sleeve 302 is inserted in the patient to locate the position of fluid supply sleeve 302 (and outer cannula 44) within the patient and relative to certain anatomical structures. The radioactive isotope may be incorporated in the elongated channel section 304 in a number of ways. In one example, the radioactive isotope is added to a molten resin used to form elongated channel section 304 and suspended within the solidified resin. In another example, elongated channel section 304 is formed with an inner and/or outer surface feature such as bores, holes, cavities, or channels and dipped into a solution containing the radioactive isotope. The isotope then wicks into the surface feature. The surface feature could also comprise a "rough" surface that defines a plurality of "valleys" in which the radioactive material would remain. In addition, the surface feature may comprise electrostatic charges to attract and hold the radioactive material through electrostatic forces.

Fluid supply sleeve 302 can be used to deliver fluids when tissue cutting device 40 is used in a tissue cutting mode or in an aspiration wand mode. In one example, a tissue removal system comprising tissue cutting device 40 with fluid supply sleeve 302 installed on the outer cannula 44 is provided. A fluid source is provided and is connected to fluid source connector 310. A valve may be provided between the fluid source and fluid source connector 310 to allow the surgeon to selectively deliver the fluid to fluid supply sleeve 302. Alternatively, a valve may be provided between fluid source connector 310 and hub 306.

The surgeon selectively positions fluid supply sleeve 302 at a desired location along the length of outer cannula 44. In one example, the surgeon grips hub 306 and advances or retracts fluid supply sleeve 302 along outer cannula 44 to the desired location. The outer cannula 44 is then inserted into the patient's body to a location proximate the target tissue. In one example, fluid is supplied from the fluid source through fluid supply line 308, into hub 306, and through fluid supply channel 312. The fluid then exits fluid supply sleeve 302 at fluid supply channel open proximal end 319 and contacts the target tissue and/or surrounding tissues proximate the target tissue. A vacuum level may then be supplied to inner cannula lumen 78 in the manner described previously. Motor 62 may be activated as described previously to cause inner cannula 76 to reciprocate within outer cannula lumen 110 and sever tissue received in outer cannula opening 49. Fluid may be supplied via fluid supply sleeve 302 before, during, and/or after reciprocation of inner cannula 76 within outer cannula lumen 110. Severed tissue snippets and/or fluids, including but not limited to the fluids supplied via the fluid supply sleeve 302, are then aspirated through inner cannula lumen 78 and into tissue collector 58 as described previously.

In certain examples, tissue cutting device 40 may be used to cut tissues with ruptured blood vessels which can cause significant bleeding. One such example is a hemangioblastoma. In such cases, a hemostatic agent or sealant of the type described previously may be supplied during or after the tissue cutting procedure to minimize blood flow.

In another exemplary method, a tissue cutting system comprising tissue cutting device 40 and fluid supply sleeve 302 is provided, and the system is used in an aspiration mode. In accordance with the example, the surgeon selectively positions the fluid supply sleeve 302 along the length of outer cannula 44 to occlude a portion of outer cannula opening 49 as best seen in FIGS. 31 and 32. The fluid supply sleeve 302 may be used to occlude a desired percent of the open area of outer cannula opening 49 and therefore to selectively adjust the aspiration provided at outer cannula opening for a given vacuum level supplied to inner cannula lumen 78. For example, fluid supply sleeve 302 positions may be selected that limit the percent open area of outer cannula opening 49 to 25%, 50%, or 75% of the total area of opening 49. A vacuum level may then be supplied to inner cannula lumen 78 and may draw surrounding tissues into the partially-occluded outer cannula opening 49. In addition, fluids may be aspirated through outer cannula opening 49, inner cannula lumen 78, tissue collector 58, and collected in fluid collection canister 192 (FIG. 21A). With tissue drawn into outer cannula opening 49, motor 62 may be activated to sever the received tissue and collect it as described previously. Thus, fluid supply sleeve 302 effectively allows the surgeon to manually adjust the degree of aspiration at outer cannula opening 49, and correspondingly, the size of the tissue samples that are received in outer cannula opening 49 and severed by inner cannula 76. Fluid may be supplied at or near the target tissue via fluid supply channel 312 before, during, and/or after tissue resection. However, fluid supply sleeve 302 may also be used to adjust the degree of aspiration provided by tissue cutting device 40 without supplying fluids.

It will be appreciated that the tissue cutting devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

The invention claimed is:

1. A temperature controlled system for tissue samples, comprising:
   a base member defined by side wall members connected to a bottom surface and an open top surface opposite the bottom surface, wherein the side walls and bottom surface that define the base member, also collectively form a reservoir that is configured to receive a temperature control medium;
   a sleeve member attached to one of the side wall members and disposed within the base member, wherein the sleeve member defines a tissue collector chamber within the sleeve member that selectively receives a tissue collector,
   wherein at least a portion of the sleeve member is in direct communication with the reservoir, wherein the tissue collector chamber is separated from the reservoir by the sleeve member such that the tissue collector chamber is not in communication with the reservoir and the temperature control medium disposed within the reservoir is prevented from entering the tissue collector chamber; and
   a tissue preservation system in fluid communication with a tissue collector operatively connected to a tissue resection device, wherein the tissue preservation system further comprises:
   a connector element having a body portion defined by first and second ends and an inlet port that intersects the body portion between the first and second ends, wherein the first end is configured to be fluidly connected to a tissue resecting device and wherein the second end is configured to be fluidly connected to a tissue collector; and
   wherein the inlet port is configured to deliver fluid from a fluid supply source into the connector element so as to deliver fluid to the tissue collector.

2. The temperature controlled system of claim 1, wherein the sleeve member has a C-shape so as to define a longitudinal slit that extends a length of the sleeve member from a top of the sleeve member to the bottom of the sleeve member and intersects an outer surface of one of the side wall members of the base member.

3. The temperature controlled system of claim 1, wherein the sleeve member is constructed of a thermally conductive material.

4. The temperature controlled system of claim 1, further comprising a selectively removable lid that is configured to selectively close the reservoir.

5. The temperature controlled system of claim 1, further comprising a temperature gauge in operative communication with the reservoir.

6. The tissue preservation system of claim 1, wherein the tissue collector further comprises a filter body, wherein the filter body includes first and second members constructed of filter material, wherein the first and second members are joined together with a hinge along a length of the first and second members, wherein the first and second members selectively engage with one another to form a collection cavity and wherein the first member and the second member may be selectively separated to facilitate access to an interior of the filter body.

7. The temperature controlled system of claim 1, wherein one of the side wall members is contoured to form a channel therein and wherein the sleeve member is disposed within the channel.

8. The temperature controlled system of claim 7, further comprising an opening formed on the side wall member that is contoured, wherein the opening opens into the channel and is in communication with the reservoir.

9. The temperature controlled system of claim 4, wherein the lid further includes an opening on the top surface that aligns with the tissue collector chamber.

10. The temperature controlled system of claim 4, wherein the lid further includes a projecting element connected to a bottom surface of the lid, wherein the projecting element is disposed inwardly from a peripheral edge of the lid and is disposed within the reservoir, when attached to the base member.

11. The temperature controlled system of claim 10, further comprising a seal member disposed around a peripheral edge of the projecting element.

12. The temperature controlled system of claim 8, wherein the opening opens directly into the reservoir.

* * * * *